United States Patent
Yonezawa et al.

(10) Patent No.: US 8,153,816 B2
(45) Date of Patent: Apr. 10, 2012

(54) PROCESS FOR PRODUCTION OF 3-[5-[4-(CYCLOPENTYLOXY)-2-HYDROXYBENZOYL]-2-[(3-OXO-2-SUBSTITUTED-2,3-DIHYDRO-1,2-BENZISOXAZOL-6-YL)METHOXY]PHENYL]PROPIONATE ESTER AND INTERMEDIATE FOR THE PROCESS

(75) Inventors: Kenji Yonezawa, Toyama (JP); Tamotsu Takamatsu, Toyama (JP); Naokatu Aoki, Toyama (JP); Tomohiro Hashimoto, Toyama (JP); Masahiro Takebayashi, Toyama (JP); Yoshiaki Suzuki, Toyama (JP); Yuji Oonishi, Toyama (JP)

(73) Assignee: Toyama Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/177,744

(22) Filed: Jul. 7, 2011

(65) Prior Publication Data

US 2011/0263866 A1 Oct. 27, 2011

Related U.S. Application Data

(62) Division of application No. 12/280,098, filed as application No. PCT/JP2007/052953 on Feb. 19, 2007, now Pat. No. 8,017,789.

(30) Foreign Application Priority Data

Feb. 21, 2006 (JP) ................................. 2006-043777
Apr. 26, 2006 (JP) ................................. 2006-121582
Apr. 26, 2006 (JP) ................................. 2006-121601

(51) Int. Cl.
*C07D 261/20* (2006.01)
(52) U.S. Cl. ...................................................... 548/241
(58) Field of Classification Search .................. None
See application file for complete search history.

(56) References Cited

U.S. PATENT DOCUMENTS

| 7,314,888 | B1 | 1/2008 | Chaki et al. |
| 2005/0113400 | A1 | 5/2005 | Chaki et al. |
| 2006/0148834 | A1 | 7/2006 | Xu et al. |

FOREIGN PATENT DOCUMENTS

| WO | 00 27792 | 5/2000 |
| WO | 03 042150 | 5/2003 |
| WO | 2004-050082 | 6/2004 |

OTHER PUBLICATIONS

Gottlieb H.E. et al, "14C Nuclear Magnetic Resources Spectroscopy of 6- and 7-Substituted Coumarins. Correlation with Hammett Constants", Journal of the Chemical Society, No. 4, pp. 435-437 (1979).
Burmester G.R., et al., "Adalimumab Clinical Trial Safety in Multiple Indications and Reduction in Mortality in Rheumatoid Arthritis," vol. 54, No. 9, pp. S232 (2006).
Harayama T. et al., "Convenient Synthesis of a Simple Coumarin from Salicylaldehyde and Wittig Reagent, II): Synthesis of Bromoand Methoxycarbonylcourmarins", Chem. Pharm. Bull. vol. 42, No. 10, pp. 2170-2173 (1994).
Papa, D., et al., "Reductions with Nickel-Aluminum Alloy and Aqueous Alkali. Part VIII. Hydrogenolysis of Furan Derivatives", Journal Org. Chem. vol. 16, pp. 253-261, (1951).
Cingolani E., et al., "Coumarin-3, 6-dicarboxylic Acids and their Derivatives", Annali Di Chimica, vol. 56, No. 6, pp. 700-716, (1966).

*Primary Examiner* — Kamal Saeed
(74) *Attorney, Agent, or Firm* — Oblon, Spivak, McClelland, Maier & Neustadt, L.L.P.

(57) ABSTRACT

A 6-(halomethyl)-1,2-benzisoxazol-3(2H)-one derivative represented by the formula:

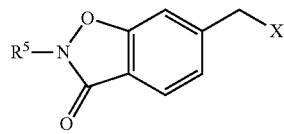

wherein $R^5$ is a methyl group that is substituted with one or more optionally substituted phenyl groups, or an optionally substituted oxygen-containing heterocyclic group; and X is a halogen atom.

9 Claims, No Drawings

PROCESS FOR PRODUCTION OF 3-[5-[4-(CYCLOPENTYLOXY)-2-HYDROXYBENZOYL]-2-[(3-OXO-2-SUBSTITUTED-2,3-DIHYDRO-1,2-BENZISOXAZOL-6-YL)METHOXY]PHENYL] PROPIONATE ESTER AND INTERMEDIATE FOR THE PROCESS

REFERENCE TO PRIOR APPLICATIONS

This application is a Divisional application of U.S. Ser. No. 12/280,098, filed Aug. 20, 2008, now allowed; which is a 371 application of PCT/JP07/52953, filed Feb. 19, 2007; and claims priority to Japanese Application Nos. 2006-043777, filed Feb. 21, 2006; 2006-121582, filed Apr. 26, 2006; and 2006-121601, filed Apr. 26, 2006.

TECHNICAL FIELD

The present invention relates to a method for preparing 3-{5-[4-(cyclopentyloxy)-2-hydroxybenzoyl]-2-[(3-oxo-2-substituted-2,3-dihydro-1,2-benzisoxazol-6-yl)methoxy]phenyl}propionic acid ester and an intermediate thereof.

BACKGROUND ART

3-{5-[4-(cyclopentyloxy)-2-hydroxybenzoyl]-2-[(3-hydroxy-1,2-benzisoxazol-6-yl)methoxy]phenyl}propionic acid (henceforth referred to as T-5224) has an excellent antiarthritic action and has an osteoclastic suppressing action, furthermore, it is very safe, has excellent pharmacokinetics and is valuable as an antirheumatic agent (Non-patent document 1).

T-5224 is prepared by deprotecting 3-{5-[4-(cyclopentyloxy)-2-hydroxybenzoyl]-2-[(3-oxo-2-substituted-2,3-dihydro-1,2-benzisoxazol-6-yl)methoxy]phenyl}propionic acid ester (henceforth, referred to as T-5224 intermediate) (Patent document 1).

The T-5224 intermediate is prepared by reacting 6-(bromomethyl)-2-(methoxymethyl)-1,2-benzisoxazol-3(2H)-one (henceforth referred to as preparation intermediate 1-1) or 6-(bromomethyl)-3-(methoxymethoxy)-1,2-benzisoxazole (henceforth referred to as preparation intermediate 1-2) with 3-{5-[4-cyclopentyloxy)-2-hydroxybenzoyl]-2-hydroxyphenyl}propionic acid methyl ester (henceforth referred to as preparation intermediate 2) (Patent document 1).

However, preparation intermediate 1-1 and preparation intermediate 1-2 both have drawbacks such as that they both (a) are oil substances and (b) have low purity and stability.

The preparation methods for the preparation intermediate 1-1 and preparation intermediate 1-2 both have drawbacks such as that they (c) require complex procedures such as silica gel column chromatography, (d) have low yield and (e) use raw materials which are dangerous and have a high toxicity (chloromethyl methyl ether).

The preparation method for preparation intermediate 2 has drawbacks such as that it (f) requires complicated procedures such as distillation and column chromatography and (g) uses extremely expensive, flammable and self-reactive reagents (azodicarbonyl compounds such as diethyl azodicarboxylate and diisopropyl azodicarboxylate), and (h) a large amount of aluminum chloride waste solution which requires complex treatments is generated.

By reacting preparation intermediate 1-1 or preparation intermediate 1-2 with preparation intermediate 2, the T-5224 intermediates that are prepared have drawbacks such as that they are all (i) oil substances, (j) and for isolating these, complex procedures such as silica gel column chromatography are required.

Using preparation intermediate 1-1, preparation intermediate 1-2, and preparation intermediate 2, the method for preparing T-5224 intermediate is not satisfactory.

Intermediate product 2 can be prepared from 2-oxo-2H-chromene carboxylic acid or a salt thereof. Examples of the preparation method of 2-oxo-2H-chromene carboxylic acid or a salt thereof include, for example, (A) a method in which after brominating 6-methyl-2H-chromen-2-one and reacting with hexamethylenetetramine, hydrolysis and oxidation are conducted (Patent document 2); (B) a method of ring-closing a cinnamic acid ester which is obtained by several processes from p-hydroxybenzoic acid or an ester thereof (Non-patent document 2); (C) a method for ring-closing of p-hydroxybenzoic acid or an ester thereof (Non-patent document 3); (D) a method in which after conducting Knoevenagel condensation of 3-formyl-4-hydroxybenzoic acid and maleic acid, heating and decarboxylating are conducted (Non-patent document 4).

However, the preparation method (A) has drawbacks such as that it (k) requires complex procedures, (l) there are many types of reagents and they are expensive.

The preparation method (B) has drawbacks such as that (m) the ring-closing reaction is at high temperatures, (n) there are many steps, and (O) there are many types of reagents and they are expensive.

Preparation method (C) has drawbacks such as that (p) it has low yield.

Preparation method (D) has drawbacks such as that (q) the starting substance is expensive and (r) the decarboxylating reaction is at high temperatures.

Methods for industrial preparation of 2-oxo-2H-chromene carboxylic acid or a salt thereof have not been satisfactory.

Patent document 1: International publication WO03/042150 pamphlet

Patent document 2: International publication WO2004/050082 pamphlet

Non-patent document 1: Arthritis Rheum, 2006 Vol. 54 (9), S232

Non-patent document 2: Chem. Pharm. Bull., 1994, Vol. 42, p. 2170-2173

Non-patent document 3: J. Org. Chem. 1951, Vol. 16, p. 253-261.

Non-patent document 4: Annali di Chimica (Rome) 1966 Vol. 56 (6), p. 700-716

There is a strong desire for a preparation method that can easily mass-prepare T-5224 using inexpensive raw materials and that is safe for human bodies and does not have a large environmental impact.

DISCLOSURE OF THE INVENTION

Under these conditions, the present inventors conducted intensive research, and as a result, they found that (1) a benzophenone derivative represented by general formula [1]:

[Formula 1]

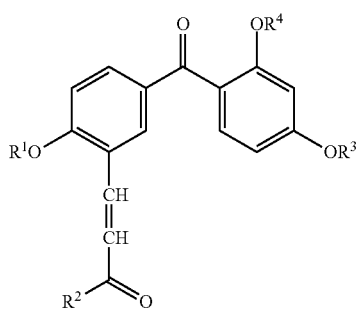

[1]

wherein $R^1$ represents a hydrogen atom and $R^2$ represents an alkoxy group, or $R^1$ and $R^2$ taken together represent a bond; $R^3$ represents a cycloalkyl group and $R^4$ represents a hydrogen atom, or $R^3$ and $R^4$ are the same and each represents a hydrogen atom or an alkyl group, provided that when $R^1$ is a hydrogen atom and $R^2$ is an alkoxy group, $R^3$ represents a cycloalkyl group and $R^4$ represents a hydrogen atom, or a salt thereof, is an important preparation intermediate in the preparation of preparation intermediate 2;

(2) a benzophenone derivative represented by general formula [2]:

[Formula 6]

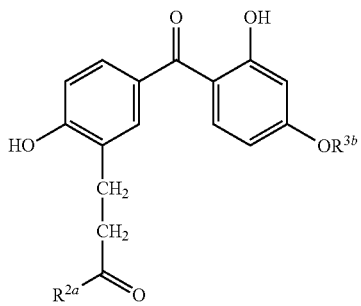

[2]

wherein $R^{2a}$ represents an alkoxy group; and $R^{3b}$ represents a cycloalkyl group, or a salt thereof, can be prepared easily by subjecting a benzophenone derivative represented by the general formula [1a]:

[Formula 2]

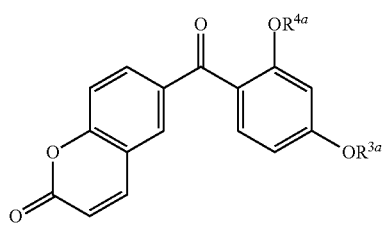

[1a]

wherein $R^{3a}$ and $R^{4a}$ represent an alkyl group, to a dealkylation reaction to give a benzophenone derivative represented by the formula [1b]:

[Formula 3]

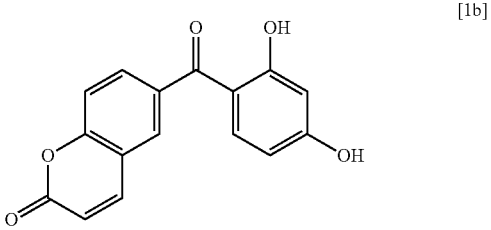

[1b]

or a salt thereof, then subjecting the benzophenone derivative or a salt thereof to an alkylation reaction in the presence of a base to give a benzophenone derivative represented by the general formula [1c]:

[Formula 4]

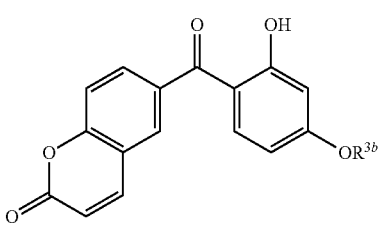

[1c]

wherein $R^{3b}$ is as defined above, or a salt thereof, then subjecting the benzophenone derivative or a salt thereof to a ring-opening reaction in the presence of a base to give a benzophenone derivative represented by the general formula [1d]:

[Formula 5]

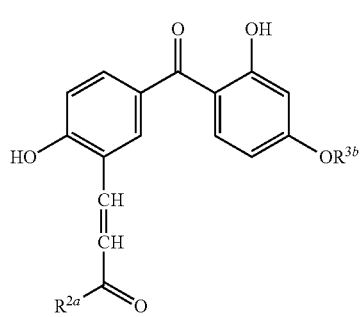

[1d]

wherein $R^{2a}$ and $R^{3b}$ are as defined above, or a salt thereof, and then subjecting the benzophenone derivative or a salt thereof to a reduction reaction;

(3) a 6-(halomethyl)-1,2-benzisoxazol-3(2H)-one derivative represented by general formula [3]:

[Formula 7]

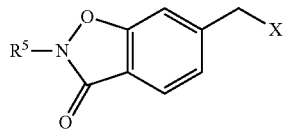

[3]

wherein $R^5$ represents a methyl group that is substituted with one or more optionally substituted phenyl groups, or an optionally substituted oxygen-containing heterocyclic group; and X represents a halogen atom, is valuable as an preparation intermediate for T-5224, and, in particular, a compound in which $R^5$ is an optionally substituted triphenylmethyl or tetrahydro-2H-pyran-2-yl group (a) is a solid that can be handled easily, (b) has a high purity and stability, (c) is prepared without using complex procedures such as silica gel column chromatography, (d) is prepared at high yield, (e) is safe for human bodies, (g) does not have a large environmental impact, (h) can be mass prepared using inexpensive raw materials, and is superior to known preparation intermediate 1-1 and preparation intermediate 1-2;

(4) a 6-(halomethyl)-1,2-benzisoxazol-3(2H)-one derivative represented by general formula [3]:

[Formula 9]

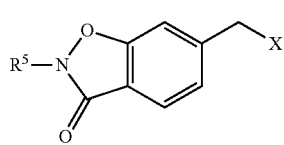

[3]

wherein $R^5$ and X are as defined above, can be prepared easily by protecting the 2 position of 6-methyl-1,2-benzisoxazol-3-ol with a methyl group that is substituted with one or more optionally substituted phenyl groups, or an optionally substituted oxygen-containing heterocyclic group to give a 6-methyl-1,2-benzisoxazol-3(2H)-one derivative represented by general formula [4]:

[Formula 8]

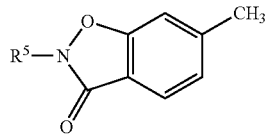

[4]

wherein $R^5$ is as described above, followed by halogenation;
(5) a 6-(halomethyl)-1,2-benzisoxazol-3(2H)-one derivative represented by general formula [3]

[Formula 13]

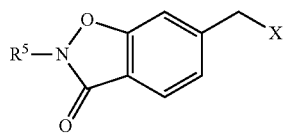

[3]

wherein $R^5$ and X are as described above, can be prepared easily by reacting a (hydroxymethyl)benzoic acid ester derivative represented by general formula [5]:

[Formula 10]

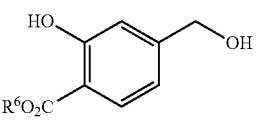

[5]

wherein $R^6$ represents an alkyl group, or a salt thereof, with hydroxylamine or a salt thereof to give a (hydroxymethyl)benzhydroxamic acid derivative represented by formula [6]:

[Formula 11]

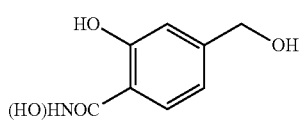

[6]

or a salt thereof, then reacting the (hydroxymethyl)benzhydroxamic acid derivative or a salt thereof with thionyl halide, then subjecting the resulting compound or a salt thereof to an intramolecular cyclization reaction in the presence of a base to give a 6-(halomethyl)-1,2-benzisoxazol-3-ol derivative represented by general formula [7]:

[Formula 12]

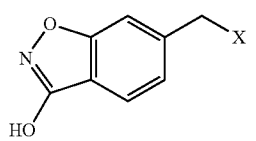

[7]

wherein X is as described above, or a salt thereof, and then protecting the 2 position of the 6-(halomethyl)-1,2-benzisoxazol-3-ol derivative or a salt thereof with a methyl group that is substituted with one or more optionally substituted phenyl groups, or an optionally substituted oxygen-containing heterocyclic group;

(6) the T-5224 intermediate prepared from the compound of general formula [2] or a salt thereof and a compound of general formula [3] is a solid that is handled easily;

(7) 2-oxo-2H-chromene carboxylic acid represented by general formula [10]

[Formula 16]

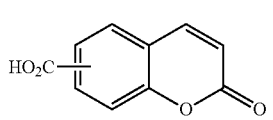

[10]

or a salt thereof, can be prepared easily by oxidizing methyl-2H-chromen-2-one represented by general formula [8]:

[Formula 14]

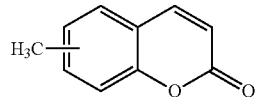

[8]

with manganese dioxide to give 2-oxo-2H-chromene carbaldehyde represented by general formula [9]:

[Formula 15]

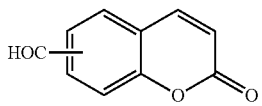

[9]

and then oxidizing the compound with a salt of halous acid, and in particular, by oxidizing the compound of general formula [8] with manganese dioxide in the presence of sulfuric acid and water, the compound of general formula [9] is prepared at high yield, and because manganese which is a side product is dissolved by the reaction solvent, no special procedure is needed to remove manganese, and furthermore, the compound of general formula [10] or a salt thereof of high purity is prepared by a simple procedure without having to isolate the compound of general formula [9], and the present invention was completed.

With the compound of the present invention and the preparation method of the present invention, T-5224 is prepared easily and at an industrial scale.

The preparation method of the present invention has the characteristics that (1) complex purification procedures such as distillation and column chromatography are not necessary, (2) reagents that are dangerous and have toxicity (azodicarbonyl compounds such as diethyl azodicarboxylate and diisopropyl azodicarboxylate; chloromethyl methyl ether) are not used, (3) reaction procedures are simple, and the like. In other words, the preparation method of the present invention is safe for human bodies and has a low environmental impact and is useful as a simple preparation method for mass preparation of T-5224.

The compound of the present invention (1) is a solid that is easily handled, (2) has high purity and stability, (3) is prepared without needing complex procedures such as silica gel column chromatography, (4) is prepared with high yield, (5) is safe for human bodies, has low environmental impact, and is capable of being mass-prepared using inexpensive raw materials.

By using the compound of the present invention, T-5224 can be prepared easily.

BEST MODE FOR CARRYING OUT THE INVENTION

The present invention is described in detail below.

As used herein, unless stated otherwise, a halogen atom means a chlorine atom, a bromine atom and an iodine atom; an alkyl group means a straight chain or branched $C_{1-6}$ alkyl group such as methyl, ethyl, propyl, isopropyl, butyl, sec-butyl, isobutyl, tert-butyl and pentyl; a cycloalkyl group means a $C_{3-8}$ cycloalkyl group such as cyclopropyl, cyclobutyl, cyclopentyl and cyclohexyl; an alkoxy group means a straight chain or branched $C_{1-6}$ alkyloxy group such as methoxy, ethoxy, propoxy, isopropoxy, butoxy, isobutoxy, sec-butoxy, tert-butoxy, pentyloxy and isopentyloxy; an alkylsulfonyloxy group means a $C_{1-6}$ alkylsulfonyloxy group, such as methylsulfonyloxy, trifluoromethylsulfonyloxy and ethylsulfonyloxy; an arylsulfonyloxy group means for example a benzenesulfonyloxy and toluenesulfonyloxy group.

Examples of the leaving group include a halogen atom, an alkylsulfonyloxy group and an arylsulfonyloxy group.

The "methyl group that is substituted with one or more optionally substituted phenyl groups" of $R^5$ is a benzyl, diphenylmethyl and triphenylmethyl group in which the phenyl group may be optionally substituted with one or more groups selected from a halogen atom, a nitro group, an alkyl group, an alkoxy group, and the like.

The "optionally substituted oxygen-containing heterocyclic group" of $R^5$ is a heterocyclic group that contains oxygen atom as a ring-forming heteroatom such as tetrahydro-2H-pyran-2-yl and tetrahydro-2H-furan-2-yl that may be optionally substituted with one or more groups selected from a halogen atom, an alkyl group, and an alkoxy group, and the like.

With respect to the compound represented by general formula [1] or a salt thereof, examples of preferred compounds are the following compounds.

Compounds in which $R^1$ is a hydrogen atom and $R^2$ is a methoxy group or an ethoxy group as well as compounds in which $R^1$ and $R^2$ taken together form a bond are preferred. Compounds in which $R^1$ is a hydrogen atom and $R^2$ is a methoxy group and compounds in which $R^1$ and $R^2$ taken together form a bond are more preferable.

Compounds in which $R^3$ and $R^4$ are the same and each is a hydrogen atom, a methyl group, or an ethyl group as well as compounds in which $R^3$ is a cycloalkyl group and $R^4$ is a hydrogen atom are preferred. Compounds in which $R^3$ and $R^4$ are the same and each is a hydrogen atom or a methyl group and compounds in which $R^3$ is a cyclopentyl group and $R^4$ is a hydrogen atom are more preferred.

When $R^1$ is a hydrogen atom and $R^2$ is an alkoxy group, compounds in which $R^3$ is a cycloalkyl group and $R^4$ is a hydrogen atom are preferred. When $R^1$ is a hydrogen atom and $R^2$ is a methoxy group or an ethoxy group, compounds in which $R^3$ is a cyclopentyl group and $R^4$ is a hydrogen atom are more preferred.

Regarding the compound represented by general formula [1] or a salt thereof, preferable salts include sodium salts.

Examples of the preferred preparation method of the compound of general formula [2] or a salt thereof include the following methods.

In the preferred preparation method, $R^{3a}$ and $R^{4a}$ of the compound of general formula [1a] are the same and each is an alkyl group; $R^{3b}$ of the compounds of general formula [1c] and [1d] is a cycloalkyl group; $R^{2a}$ of the compound of general formula [1d] is an alkoxy group.

In a more preferred preparation method, $R^{3a}$ and $R^{4a}$ of the compound of general formula [1a] are the same and each is a methyl group or an ethyl group; $R^{3b}$ of the compounds of general formula [1c] and [1d] is a cyclopentyl group; $R^{2a}$ of the compound of general formula [1d] is a methoxy group or an ethoxy group.

In a more preferred preparation method, $R^{3a}$ and $R^{4a}$ of the compound of general formula [1a] are the same and each is a methyl group; $R^{3b}$ of the compounds of general formula [1c] and [1d] is a cyclopentyl group; $R^{2a}$ of the compound of general formula [1d] is a methoxy group.

Regarding the compound represented by general formula [3], the preferred compounds include the following examples.

A compound in which $R^5$ is an optionally substituted triphenylmethyl or an optionally substituted tetrahydro-2H-pyran-2-yl group is preferred. A compound in which $R^5$ is an optionally substituted triphenylmethyl group is more preferred. A compound in which $R^5$ is a triphenylmethyl group that may be optionally substituted with a halogen atom or a methoxy group is more preferred. A compound in which $R^5$ is a triphenylmethyl group is even more preferred.

A compound in which X is a chlorine atom or a bromine atom is preferred.

Regarding the preferred method for preparing the compound of general formula [3], the following examples are given.

In a preferred preparation method, a compound in which $R^5$ is an optionally substituted triphenylmethyl or an optionally substituted tetrahydro-2H-pyran-2-yl group is used. In a more preferred preparation method, a compound in which $R^5$ is an optionally substituted triphenylmethyl group is used. In an even more preferred preparation method, a compound in which $R^5$ is a triphenylmethyl group that may be optionally substituted with a halogen atom or a methoxy group is used. In an even more preferred preparation method, a compound in which $R^5$ is a triphenylmethyl group is used. In a preferred preparation method, a compound in which X is a chlorine atom or a bromine atom is used.

Regarding the preferred preparation method for the compound of general formula [10] or a salt thereof, the following examples are given.

In a preferred preparation method, the compound of general formula [8] is oxidized with manganese dioxide in the presence of sulfuric acid and water, and after making the compound of general formula [9], this is oxidized with a salt of halous acid.

The preparation method is preferably a method in which the manganese dioxide that is used is an activated manganese dioxide.

The preparation method is preferably a method in which the concentration of sulfuric acid with respect to sulfuric acid and water is 10-990 (w/w), and more preferably it is 35-75% (w/w), and even more preferably 45-65% (w/w).

The preparation method is preferably a method in which the compound of general formula [8] is 6-methyl-2H-chromen-2-one or 7-methyl-2H-chromen-2-one, and more preferably a method in which the compound is 6-methyl-2-oxo-2H-chromene.

The compound of general formula [9] can be isolated and purified, but preferably, it advances to the next reaction without being isolated.

Regarding the method in which crystals of the compound of general formula [10] or a salt thereof are isolated, a method of crystallizing from a mixed solvent of ketones such as methyl isobutyl ketone and the like and water, a mixed solvent of alcohols such as methanol and the like and water, or a mixed solvent of sulfoxides such as dimethyl sulfoxide and the like and water is preferable. A method of crystallization from a mixed solvent of methanol and water or a mixed solvent of dimethyl sulfoxide and water is more preferred.

Regarding the preferred preparation method for the T-5224 intermediate, the following examples are given.

In a preferred preparation method, $R^{2a}$ of the compound of general formula [2] is an alkoxy group, $R^{3b}$ is a cycloalkyl group; $R^5$ of the compound of general formula [3] is an optionally substituted triphenylmethyl or tetrahydro-2H-pyran-2-yl group.

In a more preferred preparation method, $R^{2a}$ of the compound of general formula [2] is a methoxy group or an ethoxy group, $R^{3b}$ is a cyclopentyl group; $R^5$ of general formula [3] is an optionally substituted triphenylmethyl group.

In an even more preferred preparation method, $R^{2a}$ of the compound of general formula [2] is a methoxy group, $R^{3b}$ is a cyclopentyl group; $R^5$ of general formula [3] is a triphenylmethyl group.

In a preferred preparation method, X of the compound of general formula [3] is a chlorine atom or a bromine atom.

Next, the method for preparing the present invention will be described.

[Preparation Method 1]

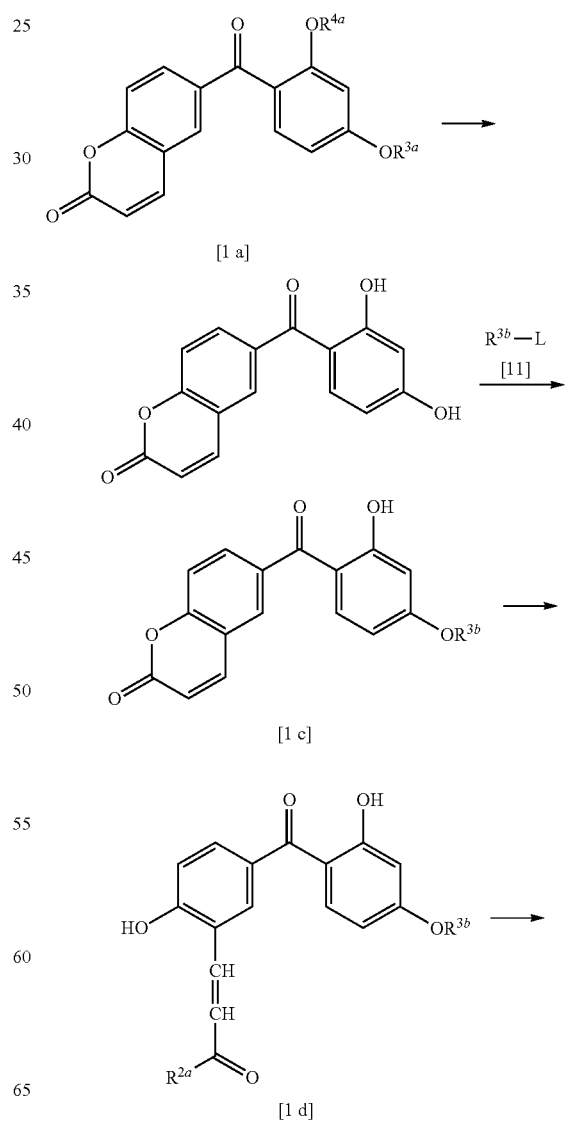

-continued

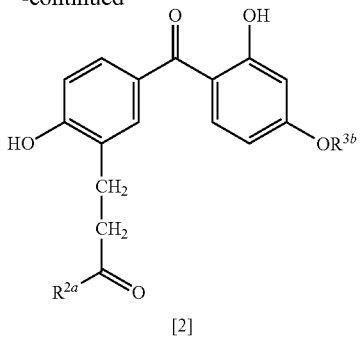

[2]

In the formula, L represents a leaving group; and $R^{2a}$, $R^{3a}$, $R^{3b}$, and $R^{4a}$ are as described above.

(1-1)

The compound of formula [1b] or a salt thereof is prepared by conducting a de-alkylating reaction on the compound of general formula [1a].

This reaction is conducted, for example, by a method described in Protective Groups In Organic Synthesis, T. W. Greene, John Wiley & Sons, Inc. 1999, third edition, p. 249-276 or a method corresponding to this method.

Examples of the solvent used for this reaction, but not particularly limited as long as it does not affect the reaction, include aliphatic hydrocarbons such as hexane and cyclohexane; aromatic hydrocarbons such as benzene, toluene, and xylene; halogenated hydrocarbons such as methylene chloride, chloroform, 1,2-dichloroethane, chlorobenzene, and dichlorobenzene; ethers such as dioxane, tetrahydrofuran, ethylene glycol dimethyl ether, and diethylene glycol dimethyl ether; sulfoxides such as dimethyl sulfoxide; esters such as methyl acetate and ethyl acetate; amides such as 1-methyl-2-pyrrolidone, N,N-dimethylformamide, and N,N-dimethylacetamide; ketones such as acetone and 2-butanone; alcohols such as methanol, ethanol, 2-propanol, and 2-methyl-2-propanol; and nitriles such as acetonitrile. These solvents can be used alone or two or more solvents can be used in combination. Preferable solvents include mixed solvents of amides and aromatic hydrocarbons. A mixed solvent of 1-methyl-2-pyrrolidone and toluene is more preferred. The usage amount of the solvent is, but not particularly limited to, preferably 1-50 times (v/w), more preferably 1-15 times (v/w) the amount of the compound of general formula [1a].

Examples of the de-alkylating agent used for this reaction include a salt of a mineral acid and an organic base. Examples of the mineral acid include hydrochloric acid, hydrobromic acid and hydroiodic acid. Examples of the organic base include dimethylaminopyridine, triethylamine and pyridine. Preferable de-alkylating agents include salts of a mineral acid and pyridine, and a salt from hydrochloric acid and pyridine is preferred. The salt is used at a molar ratio of 2-10 times, more preferably 4-10 times with respect to the compound of general formula [1a].

In addition, the salt from the mineral acid and the organic base can be generated within the reaction system. The mineral acid is used at a molar ratio of 2-10 times, more preferably 4-10 times with respect to the compound of general formula [1a]. The organic base is used at a molar ratio of 2-10 times, and more preferably 4-10 times with respect to the compound of general formula [1a].

The reaction temperature is, but not particularly limited to, 150-250° C., and preferably 180-220° C. The reaction time is not particularly limited, but is 10 minutes to 50 hours, preferably 30 minutes to 24 hours.

The compound of Formula [1b] obtained in this manner or a salt thereof can be used in the next reaction without isolating.

(1-2)

The compound of general formula [1c] or a salt thereof is prepared by conducting an alkylating reaction on a compound of formula [1b] or a salt thereof with a compound of general formula [11] in the presence of a base.

For the compound of general formula [11], as an example, cyclopentyl bromide or the like is commercially available.

Examples of the solvent used for this reaction, but not particularly limited as long as it does not affect the reaction, include aromatic hydrocarbons such as benzene, toluene, and xylene; ethers such as dioxane, tetrahydrofuran, ethylene glycol dimethyl ether, and diethylene glycol dimethyl ether; amides such as 1-methyl-2-pyrrolidone, N,N-dimethylformamide, and N,N-dimethylacetamide; ketones such as acetone and 2-butanone; and halogenated hydrocarbons such as methylene chloride, chloroform, 1,2-dichloroethane, chlorobenzene, and dichlorobenzene. These solvents can be used alone or two or more solvents can be used in combination. Preferable solvents include amides, and N,N-dimethylformamide is further preferred. The usage amount of the solvent is, but not particularly limited to, preferably 1-50 times (v/w), more preferably 1-15 times (v/w) the amount of the compound of formula [1b] or a salt thereof.

Examples of the base used for this reaction include an organic base such as dimethylaminopyridine, triethylamine, and pyridine; alkali metal hydride such as sodium hydride; and alkali metal carbonate such as potassium carbonate and sodium carbonate. Preferable bases include alkali metal carbonates such as potassium carbonate and sodium carbonate, and potassium carbonate is more preferred. The base is used at a molar ratio of 0.5-20 times, preferably 0.5-5 times with respect to the compound of formula [1b] or a salt thereof.

The compound of general formula [11] is used for this reaction at a molar ratio of 1-20 times, preferably 1-5 times with respect to the compound of formula [1b] or a salt thereof.

The reaction temperature is not particularly limited but is 0 to 120° C., preferably 50 to 120° C.

The reaction time is not particularly limited but is 10 minutes to 50 hours and is preferably 30 minutes to 24 hours.

The compound of general formula [1c] obtained in this manner or a salt thereof can be isolated and purified, but it is preferably used in the next reaction without isolating.

(1-3)

The compound of general formula [1d] or a salt thereof is prepared by a ring-opening reaction of the compound of general formula [1c] or a salt thereof in the presence of a base.

Examples of the solvent used for this reaction, but not particularly limited as long as it does not affect the reaction include aromatic hydrocarbons such as benzene, toluene, and xylene; ethers such as dioxane, tetrahydrofuran, ethylene glycol dimethyl ether, and diethylene glycol dimethyl ether; esters such as methyl acetate and ethyl acetate; ketones such as acetone and 2-butanone; alcohols such as methanol, ethanol, 2-propanol, and 2-methyl-2-propanol; nitriles such as acetonitrile; amides such as 1-methyl-2-pyrrolidone, N,N-dimethylformamide and N,N-dimethylacetamide; halogenated hydrocarbons such as methylene chloride, chloroform, 1,2-dichloroethane, chlorobenzene, and dichlorobenzene. These solvents can be used alone or two or more solvents can be used in combination. Preferable solvents include mixed solvents of alcohols and aromatic hydrocarbons, and a mixed solvent of methanol and toluene is further preferred. The usage amount of the solvent is, but not particularly limited to, preferably 1-50 times (v/w), more preferably 1-15 times (v/w) the amount of the compound of general formula [1c] or a salt thereof.

Examples of the base used for this reaction include metal alkoxides such as sodium methoxide, sodium ethoxide, potassium tert-butoxide, and sodium tert-butoxide. Preferred bases include sodium methoxide and sodium ethoxide, and sodium methoxide is more preferred. The base is used at a molar ratio of 1-20 times, preferably 1-5 times with respect to the compound of general formula [1c] or a salt thereof. The base can be dissolved in an organic solvent and used. If the base to be used is sodium methoxide, it is preferably dissolved in methanol and used. When the base that is used is sodium ethoxide, it is preferably dissolved in ethanol and used.

The reaction temperature is not particularly limited but is 0 to 100° C., preferably 30 to 80° C.

The reaction time is not particularly limited but is 10 minutes to 50 hours and is preferably 30 minutes to 24 hours.

The compound of general formula [1d] obtained in this manner or a salt thereof is preferably isolated as a sodium salt, but it can be used in the next reaction without isolating.

(1-4)

The compound of general formula [2] or a salt thereof is prepared by a reduction reaction conducted on the compound of general formula [1d] or a salt thereof.

For the reduction reaction, examples include a catalytic hydrogenation using a catalyst in the presence of a hydrogen source.

Examples of the solvent used for this reaction, but not particularly limited as long as it does not affect the reaction, include alcohols such as methanol, ethanol, 2-propanol, and 2-methyl-2-propanol; amides such as 1-methyl-2-pyrrolidone, N,N-dimethylformamide, and N,N-dimethylacetamide; halogenated hydrocarbons such as methylene chloride, chloroform, 1,2-dichloroethane, chlorobenzene, and dichlorobenzene; aromatic hydrocarbons such as benzene, toluene, and xylene; ethers such as dioxane, tetrahydrofuran, ethylene glycol dimethyl ether, and diethylene glycol dimethyl ether; nitriles such as acetonitrile; ketones such as acetone and 2-butanone; esters such as methyl acetate and ethyl acetate; carboxylic acids such as acetic acid and water. These solvents can be used alone or two or more solvents can be used in combination. Preferable solvents include a mixed solvent of water and one or more solvents selected from the group consisting of alcohols, ketones, and ethers. A mixed solvent of 2-propanol and water is more preferred. The usage amount of the solvent is, but not particularly limited to, preferably 1-50 times (v/w), more preferably 1-15 times (v/w) the amount of the compound of general formula [1d] or a salt thereof.

Examples of the catalyst used for this reaction include palladium catalysts such as palladium carbon, palladium chloride, palladium acetate, and palladium black; nickel catalysts such as Raney nickel; and platinum oxide. The amount of catalyst to be used is 0.01-1 times (w/w), preferably 0.01-0.5 times (w/w) the amount of compound of general formula [1d] or a salt thereof.

Examples of the hydrogen source to be used for this reaction include hydrogen; formic acid; formates such as sodium formate and ammonium formate, and sodium hypophosphite. Hydrogen, formic acid and formates are preferred hydrogen sources. Formic acid and formates are more preferred. Formic acid, sodium formate, and ammonium formate are even more preferred.

When formic acid or formates is used as the hydrogen source, the formic acid or formates is used at a molar ratio of 1-20 times, preferably 1-5 times with respect to the compound of general formula [1d] or a salt thereof.

When hydrogen is used as the hydrogen source, the hydrogen pressure is 1-30 atmospheres and is preferably 1-10 atmospheres.

Furthermore, an acid is preferably added in this reaction in order to suppress by-products. Examples of the acid include organic acids such as acetic acid and formic acid and mineral acids such as hydrochloric acid and sulfuric acid. The acid is used at a molar ratio of 1-20 times, preferably 1-5 times with respect to the compound of general formula [1d] or a salt thereof.

The reaction temperature is not particularly limited but is 0 to 100° C., preferably 30 to 80° C.

The reaction time is not particularly limited but is 10 minutes to 50 hours and is preferably 30 minutes to 24 hours.

[Preparation Method 2]

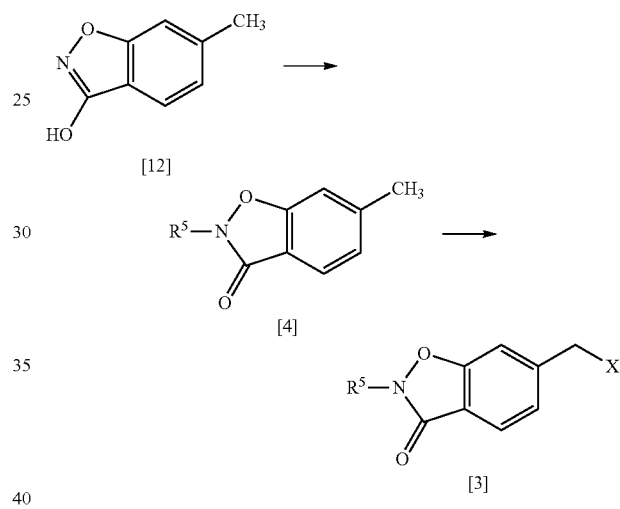

In the formula, $R^5$ and X are as defined above.

(2-1)

The compound of general formula [4] is prepared by protecting the 2 position of the compound of formula [12] or a salt thereof with a methyl group that is substituted with one or more optionally substituted phenyl groups or with an optionally substituted oxygen-containing heterocyclic group.

The compound of formula [12] or a salt thereof is prepared by a method described in International publication WO03/042150 pamphlet or US Patent application publication No. 2005/0143434, for example. Furthermore, the compound of formula [12] or a salt thereof can be prepared by the preparation method A described later.

When $R^5$ is a triphenylmethyl group that can be substituted, the compound of general formula [4] is, for example, prepared by a method described in Protective Groups In Organic Synthesis, T. W. Greene, John Wiley & Sons Inc., 1999, third edition, p. 86-113, 573-586.

Stated more concretely, in the presence of a base, the compound of formula [12] or a salt thereof is reacted with a triphenylmethyl halide.

Examples of the base used for this reaction include organic bases such as dimethylaminopyridine, triethylamine, pyridine, and N-methylmorpholine, and alkali metal carbonates such as potassium carbonate and sodium carbonate. For the base, an organic base is preferred, and pyridine is more preferred. The base is used at a molar ratio of 1-20 times, preferably 1-10 times with respect to the compound of formula [12] or a salt thereof.

Examples of the triphenylmethyl halide to be used for this reaction include triphenylmethyl chloride, triphenylmethyl bromide, (4-methoxyphenyl)diphenylmethyl chloride, (4,4'-dimethoxyphenyl)phenylmethyl chloride and (2-chlorophenyl)diphenylmethyl chloride. Triphenylmethyl chloride and triphenylmethyl bromide are preferred, and triphenylmethyl chloride is more preferred. The triphenylmethyl halide is used at a molar ratio of 1-10 times, preferably 1-3 times with respect to the compound of formula [12] or a salt thereof.

Examples of the solvent used for this reaction, but not particularly limited as long as it does not affect the reaction, include nitriles such as acetonitrile; aromatic hydrocarbons such as benzene, toluene, xylene, and mesitylene; ethers such as dioxane, tetrahydrofuran, anisole, ethylene glycol dimethyl ether, and diethylene glycol dimethyl ether; aliphatic hydrocarbons such as hexane and cyclohexane; halogenated hydrocarbons such as chloroform, methylene chloride, chlorobenzene, and dichlorobenzene; esters such as methyl acetate, ethyl acetate, and butyl acetate; amides such as N,N-dimethylformamide, and N,N-dimethylacetamide; and sulfoxides such as dimethyl sulfoxide. These can be used in combination. Preferable solvents include halogenated hydrocarbons, and methylene chloride is more preferred. The usage amount of the solvent is, but not particularly limited to, preferably 1-50 times (v/w), more preferably 1-15 times (v/w) the amount of the compound of formula [12] or a salt thereof.

The reaction temperature is not particularly limited but is −50 to 150° C., preferably −30 to 100° C.

The reaction time is not particularly limited but is 5 minutes to 50 hours and is preferably 5 minutes to 24 hours.

When $R^5$ is a tetrahydro-2H-pyran-2-yl group that can be substituted, the compound of general formula [4] is, for example, prepared by a method described in Protective Groups In Organic Synthesis, T. W. Greene, John Wiley & Sons Inc., 1999, third edition, p. 27-58, 249-280.

Stated more concretely, for example, the compound of formula [12] or a salt thereof is reacted with a dihydropyran in the presence of a catalyst.

Examples of a catalyst used for this reaction include acids such as hydrochloric acid, sulfuric acid, and p-toluenesulfonic acid; salts such as pyridinium p-toluenesulfonate, triphenylphosphine hydrobromide, copper chloride (I), aluminum sulfate, and zeolite. Preferable catalysts include salts, and pyridinium p-toluenesulfonate is more preferred. The catalyst is used at a molar ratio of 0.01-10 times, preferably 0.01-3 times with respect to the compound of formula [12] or a salt thereof.

Examples of a dihydropyran used for this reaction include 3,4-dihydro-2H-pyran, 3,4-dihydro-2-methoxy-2H-pyran, and 5,6-dihydro-4-methoxy-2H-pyran. 3,4-Dihydro-2H-pyran is preferred. The dihydropyran is used at a molar ratio of 1-20 times, preferably 1-5 times with respect to the compound of formula [12] or a salt thereof.

Examples of the solvent used for this reaction, but not particularly limited as long as it does not affect the reaction, include aromatic hydrocarbons such as benzene, toluene, xylene, and mesitylene; ethers such as dioxane, tetrahydrofuran, anisole, ethylene glycol dimethyl ether, and diethylene glycol dimethyl ether; esters such as methyl acetate, ethyl acetate, and butyl acetate; nitriles such as acetonitrile; amides such as N,N-dimethylformamide, and N,N-dimethylacetamide; and halogenated hydrocarbons such as chloroform, methylene chloride, chlorobenzene, and dichlorobenzene, and the like. These can be used in combination. Preferable solvents include halogenated hydrocarbons, and methylene chloride is more preferred. The usage amount of the solvent is, but not particularly limited to, preferably 1-50 times (v/w), more preferably 1-15 times (v/w) the amount of the compound of formula [12] or a salt thereof.

The reaction temperature is not particularly limited but is −50 to 100° C., preferably −30 to 50° C.

The reaction time is not particularly limited but is 5 minutes to 50 hours and is preferably 5 minutes to 24 hours.

The compound of general formula [4] obtained in this manner can be used in the next reaction without isolating.

(2-2)

The compound of general formula [3] is prepared by halogenating the compound of general formula [4].

Examples of halogenating agent used for the reaction, but not particularly limited as long as it is a halogenating agent that can be used for halogenating the alkyl side chain of an aromatic compound, include elementary halogens such as chlorine, bromine, and iodine; imides such as N-chlorosuccinimide, N-bromosuccinimide, N-chlorophthalimide, and N-bromophthalimide; hydantoins such as 1,3-dibromo-5,5-dimethyl hydantoin and 1,3-dichloro-5,5-dimethyl hydantoin; and sulfuryl chloride. Preferred halogenating agents include imides, and N-bromosuccinimide is more preferred. The halogenating agent is used, but not particularly limited, at a molar ratio of 1 or greater times, preferably 1-3 times with respect to the compound of general formula [4].

This reaction is preferably conducted in the presence of a radical initiator. Examples of radical initiator, but not limited as long as it is a common radical initiator, include dialkyl peroxides such as di-tert-butyl peroxide, di-tert-amyl peroxide, and di(2-methyl-2-pentyl)peroxide; diacyl peroxides such as dibenzoyl peroxide, dicumyl peroxide, and diphthaloyl peroxide; alkyl hydroperoxides such as tert-butyl hydroperoxide and cumyl hydroperoxide; percarboxylic acids, such as perbenzoic acid, monoperoxyphthalic acid, performic acid, and peracetic acid; inorganic peroxo compounds such as persulfuric acid; and organic azo compounds such as 2,2'-azobisisobutyronitrile, 2,2'-azobis(2,4-dimethyl valeronitrile), 2,2'-azobis(2-methyl butyronitrile), 2,2'-azobisisovaleronitrile, 1,1'-azobis(cyclohexane carbonitrile), 2,2'-azobis(4-methoxy-2,4-dimethyl valeronitrile), 2,2'-azobis(2-amidinopropane)dihydrochloride, and dimethyl 2,2'-azobisisobutyrate. Organic azo compounds are the preferred radical initiators, and more preferred is 2,2'-azobisisobutyronitrile, 2,2'-azobis(2,4-dimethyl valeronitrile), and 2,2'-azobis(4-methoxy-2,4-dimethyl valeronitrile). The radical initiators are used, but not limited, at a molar ratio of 0.01 or greater times, preferably 0.05-1 times with respect to the compound of general formula [4].

Examples of the solvent used for this reaction, but not particularly limited as long as it does not affect the reaction, include aliphatic hydrocarbons such as hexane, cyclohexane and heptane; ethers such as dioxane, tetrahydrofuran, anisole, ethylene glycol dimethyl ether, and diethylene glycol dimethyl ether; esters such as methyl acetate, ethyl acetate, and butyl acetate; halogenated hydrocarbons such as chloroform, methylene chloride, chlorobenzene, and dichlorobenzene. These can be used in combination. Preferred solvents include esters and halogenated hydrocarbons. Methylene chloride and chlorobenzene are more preferred. The usage amount of the solvent is, but not particularly limited to, preferably 1-50 times (v/w), more preferably 1-15 times (v/w) the amount of the compound of general formula [4].

The reaction temperature is not particularly limited but is 0 to 200° C., preferably 0 to 100° C.

The reaction time is not particularly limited but is 5 minutes to 50 hours and is preferably 5 minutes to 24 hours.

In this reaction, there may be by-product compounds in which the methyl group of the compound of general formula [4] is di-halogenated and tri-halogenated. In this case, for example, with the method described in Synthesis, 2001, Vol. 14, p. 2078-2080, and stated more concretely, by reacting a dialkyl phosphonic acid ester in the presence of a base, the compound in which the methyl group is di-halogenated or tri-halogenated can be converted to a compound of general formula [3].

Examples of the base used for this reaction include organic bases such as triethylamine, N,N-diisopropylethylamine; hydroxides of alkali metals or alkali earth metals such as sodium hydroxide, potassium hydroxide, lithium hydroxide, cesium hydroxide, and barium hydroxide; carbonates of alkali metals or alkali earth metals such as sodium carbonate, potassium carbonate, and barium carbonate. Preferred bases include carbonates of alkali metals or alkali earth metals, and potassium carbonate is more preferred. The base is used at a molar ratio of 0.5 or greater times, preferably 0.5-10 times with respect to the compound of general formula [4].

Examples of the dialkyl phosphonic acid ester used for this reaction include dimethyl phosphonic acid ester, diethyl phosphonic acid ester, diisopropyl phosphonic acid ester, and dibutyl phosphonic acid ester; dimethyl phosphonic acid ester and diethyl phosphonic acid ester are preferred. The dialkyl phosphonic acid ester is used at a molar ratio of 0.5 or greater times, preferably 0.5-10 times with respect to the compound of general formula [4].

Examples of the solvent used for this reaction, but not particularly limited as long as it does not affect the reaction, include ethers such as dioxane, tetrahydrofuran, anisole, ethylene glycol dimethyl ether, and diethylene glycol dimethyl ether; and halogenated hydrocarbons such as methylene chloride, chloroform, 1,2-dichloroethane, chlorobenzene, and dichlorobenzene. These can be used in combination. Preferred solvents include halogenated hydrocarbons. Methylene chloride is more preferred. The usage amount of the solvent is, but not particularly limited to, preferably 1-50 times (v/w), more preferably 1-20 times (v/w) the amount of the compound of general formula [4].

The reaction temperature is not particularly limited but is 0 to 200° C., preferably 0 to 100° C.

The reaction time is not particularly limited but is 1 to 50 hours and is preferably 1 to 24 hours.

[Preparation Method 3]

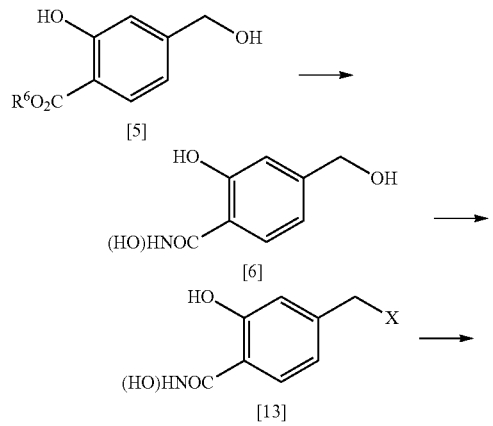

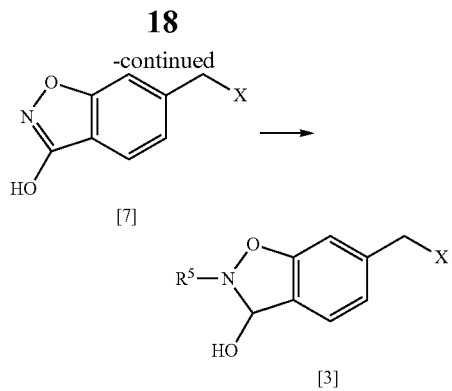

In the formula, $R^5$, $R^6$, and X are as defined above.

As an example of the compound of general formula [5] or a salt thereof, 2-hydroxy-4-(hydroxymethyl)benzoic acid methyl ester is known. In addition, the compound of general formula [5] or a salt thereof is prepared by, for example, a method described in International publication WO2004/113281 pamphlet or Japanese Patent No. 3197011.

Furthermore, the compound of general formula [5] or a salt thereof is prepared by a preparation method B described later.

(3-1)

The compound of formula [6] or a salt thereof is prepared by reacting the compound of general formula [5] or a salt thereof with hydroxylamine or a salt thereof in the presence of or in the absence of a base.

Examples of the hydroxylamine or a salt thereof used for this reaction include hydroxylamine, hydroxylamine hydrosulfate, hydroxylamine hydrochloride, and hydroxylamine oxalate. Hydroxylamine hydrochloride is preferred. Hydroxylamine or a salt thereof can be dissolved in a solvent such as water and methanol and used. The hydroxylamine or a salt thereof is used at a molar ratio of 1 or greater times, preferably 1-5 times with respect to the compound of general formula [5] or a salt thereof.

This reaction is preferably conducted in the presence of a base. Examples of the base include hydroxides of alkali metals or alkali earth metals such as sodium hydroxide, potassium hydroxide, lithium hydroxide, cesium hydroxide, and barium hydroxide; hydrogencarbonates of alkali metals such as sodium hydrogencarbonate and potassium hydrogencarbonate; carbonates of alkali metals or alkali earth metals such as sodium carbonate, potassium carbonate, barium carbonate; aluminate compounds such as sodium aluminate and potassium aluminate; metal alkoxides such as sodium methoxide, sodium ethoxide, and potassium tert-butoxide. With these, two or more types can be used in combination. In addition, if necessary, the base can be dissolved in a solvent such as water and methanol and used. Preferable bases include metal alkoxides. Sodium methoxide is more preferred. When sodium methoxide is used as the base, this is preferably used as a methanol solution. The base is used at a molar ratio of 1 or greater times, preferably 1-10 times with respect to the compound of general formula [5] or a salt thereof.

Examples of the solvent used for this reaction, but not particularly limited as long as it does not affect the reaction, include aromatic hydrocarbons such as benzene, toluene, xylene, and mesitylene; ethers such as dioxane, tetrahydrofuran, anisole, ethylene glycol dimethyl ether, and diethylene glycol dimethyl ether; halogenated hydrocarbons such as chloroform, methylene chloride, chlorobenzene, and dichlorobenzene; alcohols such as methanol, ethanol, propanol, 2-propanol, and butanol; amides such as N,N-dimethylformamide and N,N-dimethylacetamide; and water. These can be used in combination. Preferred solvents include alcohols, and methanol is more preferred. The usage amount of the solvent is, but not particularly limited to, preferably 1-50 times (v/w), more preferably 1-15 times (v/w) the amount of the compound of general formula [5] or a salt thereof.

The reaction temperature is not particularly limited but is 0 to 200° C., preferably 0 to 100° C.

The reaction time is not particularly limited but is 5 minutes to 50 hours and is preferably 5 minutes to 24 hours.

The compound of formula [6] or a salt thereof obtained in this manner can be used in the next reaction without isolating, but it is preferably isolated.

(3-2)

The compound of general formula [13] or a salt thereof is prepared by reacting the compound of formula [6] or a salt thereof with a thionyl halide.

Examples of the thionyl halide to be used for this reaction include thionyl chloride and thionyl bromide, and thionyl chloride is preferred. The thionyl halide is used at a molar ratio of 1 or greater times, preferably 1-10 times with respect to the compound of formula [6] or a salt thereof.

Examples of the solvent used for this reaction, but not particularly limited as long as it does not affect the reaction, include aromatic hydrocarbons such as benzene, toluene, xylene, and mesitylene; ethers such as dioxane, tetrahydrofuran, anisole, ethylene glycol dimethyl ether, and diethylene glycol dimethyl ether; halogenated hydrocarbons such as chloroform, methylene chloride, chlorobenzene, and dichlorobenzene; and sulfolane. These can be used in combination. Preferred solvents include halogenated hydrocarbons, and methylene chloride is more preferred. The usage amount of the solvent is, but not particularly limited to, preferably 1-50 times (v/w), more preferably 1-15 times (v/w) the amount of the compound of formula [6] or a salt thereof.

This reaction is preferably conducted in the presence of a catalyst. Examples of the catalyst include N,N-dimethylformamide. The catalyst is used at a molar ratio of 0.001-1 time, preferably 0.01-0.5 times with respect to the compound of formula [6] or a salt thereof.

The reaction temperature is not particularly limited but is 0 to 100° C., preferably 0 to 50° C.

The reaction time is not particularly limited but is 5 minutes to 50 hours and is preferably 5 minutes to 24 hours.

The compound of general formula [13] or a salt thereof obtained in this manner is preferably used in the next reaction without isolating.

(3-3)

The compound of general formula [7] or a salt thereof is prepared by reacting the compound of general formula [13] or a salt thereof with a thionyl halide and then conducting an intramolecular cyclization reaction in the presence of a base.

Examples of the thionyl halide to be used for this reaction include thionyl chloride and thionyl bromide, and thionyl chloride is preferred. The thionyl halide is used at a molar ratio of 1 or greater times, preferably 1-10 times with respect to the compound of formula [13] or a salt thereof.

Examples of the base used for this reaction include organic bases such as triethylamine, N,N-diisopropylethylamine, pyridine, dimethylaminopyridine, N-methylmorpholine, and 1,8-diazabicyclo[5.4.0]undec-7-ene (DBU); and inorganic bases such as sodium hydroxide, potassium hydroxide, sodium carbonate, and potassium carbonate. Preferable bases are organic bases, and pyridine is more preferred. The base is used at a molar ratio of 1 or greater times, preferably 1-5 times with respect to the compound of general formula [13] or a salt thereof.

Examples of the solvent used for this reaction, but not particularly limited as long as it does not affect the reaction, include aromatic hydrocarbons such as benzene, toluene, xylene, and mesitylene; ethers such as dioxane, tetrahydrofuran, anisole, ethylene glycol dimethyl ether, and diethylene glycol dimethyl ether; halogenated hydrocarbons such as chloroform, methylene chloride, chlorobenzene, and dichlorobenzene; and sulfolane. These can be used in combination. Preferred solvents include halogenated hydrocarbons, and methylene chloride is more preferred. The usage amount of the solvent is, but not particularly limited to, preferably 1-50 times (v/w), more preferably 1-15 times (v/w) the amount of the compound of general formula [13] or a salt thereof.

The reaction temperature is not particularly limited but is 0 to 100° C., preferably 0 to 50° C.

The reaction time is not particularly limited but is 5 minutes to 50 hours and is preferably 5 minutes to 24 hours.

The compound of general formula [7] or a salt thereof obtained in this manner is preferably used in the next reaction without isolating.

(3-4)

The compound of general formula [3] is prepared by protecting the 2 position of the compound of general formula [7] or a salt thereof with a methyl group that is substituted with one or more optionally substituted phenyl groups or with an optionally substituted oxygen-containing heterocyclic group. This reaction is conducted according to the preparation method (2-1).

[Preparation Method 4]

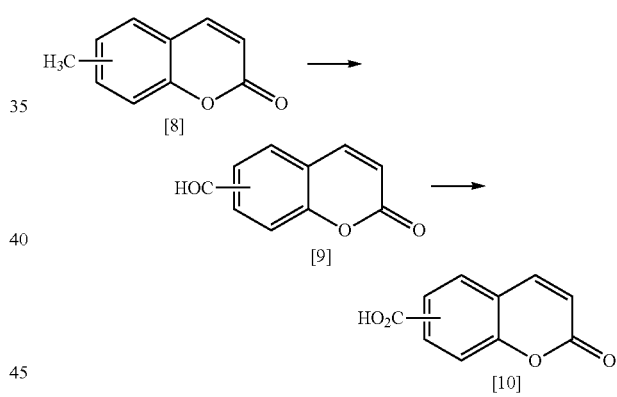

(4-1)

The compound of general formula [9] is prepared by oxidizing the compound of general formula [8] with manganese dioxide in the presence of sulfuric acid and water.

Regarding the compound of general formula [8], 6-methyl-2H-chromen-2-one is commercially available for example.

The amount of sulfuric acid and water to be used for this reaction is not particularly limited, but preferably is 1-50 times (v/w), more preferably 3-15 times (v/w) the amount of the compound of general formula [8]. The sulfuric acid concentration with respect to sulfuric acid and water is preferably 10-99% (w/w), more preferably 35-75% (w/w), and even more preferably 45-65% (w/w).

A solvent that does not affect the reaction can be added. Examples of the solvent, but not limited as long as it does not affect the reaction, include aliphatic halogenated hydrocarbons such as methylene chloride, chloroform, and dichloroethane; and aromatic halogenated hydrocarbons such as chlorobenzene and dichlorobenzene. These can be used in combination. Preferred solvents include aromatic halogenated hydrocarbons, and chlorobenzene is more preferred. The usage amount of the solvent is, but not particularly limited to, preferably 0.1 to 10 times (v/w), and more preferably 0.5 to 3 times (v/w) the amount of the compound of general formula [8].

The manganese dioxide used for this reaction is not particularly limited, but activated manganese dioxide is preferred. Activated manganese dioxide can be obtained by known methods in which, for example, manganese sulfate and potassium permanganate are reacted. In addition, commercially available activated manganese dioxide can be used, and that which is industrially mass-prepared for use in batteries can be used.

The usage amount of the manganese dioxide is 0.5 to 10 times (w/w), and more preferably 1 to 3 times (w/w) the amount of the compound of general formula [8].

The manganese dioxide can be added at one time, but preferably it is added in 2-50 aliquots, and more preferably, it is added in 8-20 aliquots.

The reaction temperature is not particularly limited but is 0 to 150° C., preferably 50 to 90° C.

The reaction time is not particularly limited but is 10 minutes to 50 hours and is preferably 30 minutes to 20 hours.

The compound of general formula [9] obtained in this manner is preferably used in the next reaction without isolating.
(4-2)

The compound of general formula [10] or a salt thereof is prepared by oxidizing the compound of general formula [9] with a salt of halous acid.

Examples of the solvent used for this reaction, but not particularly limited as long as it does not affect the reaction, include aliphatic halogenated hydrocarbons such as methylene chloride, chloroform, and dichloroethane; aromatic halogenated hydrocarbons such as chlorobenzene and dichlorobenzene; ethers such as dioxane, tetrahydrofuran, ethylene glycol dimethyl ether, and diethylene glycol dimethyl ether; amides such as N,N-dimethylformamide, N,N-dimethylacetamide, and 1-methyl-2-pyrrolidone; sulfoxides such as dimethyl sulfoxide; alcohols such as methanol, ethanol, propanol, 2-propanol, and butanol; ketones such as acetone and 2-butanone; nitriles such as acetonitrile; esters such as methyl acetate and ethyl acetate; nitro compounds such as nitromethane and nitrobenzene; aromatic hydrocarbons such as benzene, toluene, and xylene; and water. These solvents can be used in combination. Preferred solvents include a mixed solvent of ketones, sulfoxides and water, and a mixed solvent of 2-butanone, dimethyl sulfoxide, and water is more preferred. The usage amount of the solvent is, but not particularly limited to, preferably 1-50 times (v/w), and more preferably 3-30 times (v/w) the amount of the compound of general formula [9].

Examples of the salt of halous acid used for this reaction include chlorite, bromite, and iodite. Examples of the salt include alkali metal salts such as of sodium and potassium and alkali earth metal salts such as calcium. Stated more concretely, chlorite is preferred, and an alkali metal chlorite is more preferred and sodium chlorite is even more preferred. These salts can be used as an aqueous solution.

The salt of halous acid is used at a molar ratio of 1 or greater times, preferably 1-2 times with respect to the compound of general formula [9].

In general, this reaction is preferably conducted in the presence of one or more halogen scavengers selected from the group of dimethyl sulfoxide, sulfamic acid, hydrogen peroxide and 2-methyl-2-butene and the like. Preferable halogen scavengers include dimethyl sulfoxide.

The amount of halogen scavenger to be used is 0.4 times the amount (v/w), preferably 0.4 to 4 times (v/w) or greater times with respect to the compound of general formula [9].

Furthermore, this reaction is preferably conducted under acidic conditions by adding an acid or buffering agent and is more preferably conducted at pH 4.0 to 7.0. For the acid, examples include organic acids such as acetic acid and formic acid and mineral acids such as hydrochloric acid and sulfuric acid. Mineral acids such as hydrochloric acid and sulfuric acid are preferred, and hydrochloric acid is more preferred. For the buffering agent, examples include sodium dihydrogenphosphate or potassium dihydrogenphosphate.

In addition, when the compound of general formula [9] is used for this reaction without being isolated, this reaction can have a base added and is conducted at pH 4.0 to 7.0. For the base, examples include organic bases such as triethylamine and N,N-diisopropylethylamine; hydroxides of alkali metals or alkali earth metals such as sodium hydroxide, potassium hydroxide, lithium hydroxide, cesium hydroxide, and barium hydroxide; and ammonia water. The preferred bases include sodium hydroxide, potassium hydroxide and ammonia water, and ammonia water is more preferred.

The reaction temperature is not particularly limited but is −20 to 120° C., preferably 0 to 50° C.

The reaction time is not particularly limited but is 10 minutes to 50 hours and is preferably 30 minutes to 20 hours.
[Preparation Method 5]

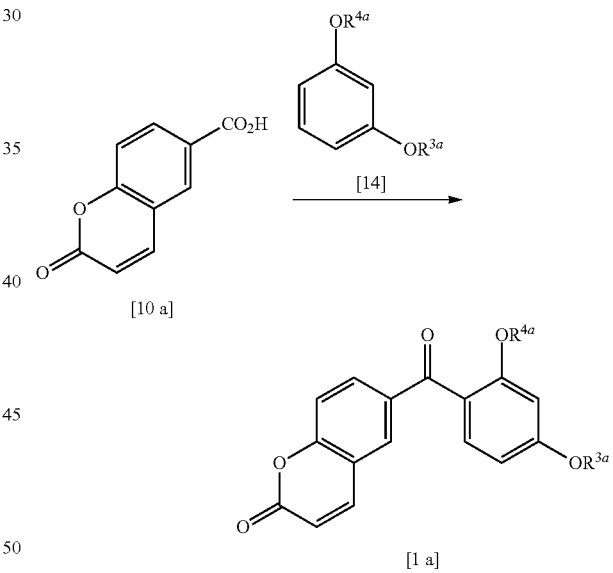

In the formula, $R^{3a}$ and $R^{4a}$ are as described above.

Regarding the compound of general formula [14], 1,3-dimethoxybenzene and 1,3-diethoxybenzene are commercially available for example.
(5-1)

The compound of general formula [1a] is prepared by reacting the compound of formula [10a] or a salt thereof with the compound of general formula [14] in the presence of an acid.

Examples of the acid to be used for this reaction include strong organic acids such as methanesulfonic acid, trifluoromethanesulfonic acid, and a mixture of methanesulfonic acid and diphosphorus pentoxide. The mixture of methanesulfonic acid and diphosphorus pentoxide is more preferred. With the mixture of methanesulfonic acid and diphosphorus pentoxide, the amount of methanesulfonic acid that is used is 1-50 times (v/w), preferably 2-20 times (v/w) the amount of the compound of formula [10a] or a salt thereof. The diphosphorus pentoxide is used at a molar ratio of 0.5-10 times, preferably a molar ratio of 0.5-4 times with respect to the compound of formula [10a] or a salt thereof.

A solvent that does not affect the reaction can be added. The solvent is not particularly limited as long as it does not affect the reaction. However, examples include halogenated hydrocarbons such as methylene chloride, chloroform, 1,2-dichloroethane, chlorobenzene, and dichlorobenzene; aliphatic hydrocarbons such as hexane and cyclohexane; nitro compounds such as nitromethane and nitrobenzene; and carbon disulfide. With these solvents, one type can be used or two or more can be used in combination. Preferred solvents include halogenated hydrocarbons, and chlorobenzene is more preferred. The usage amount of the solvent is, but not particularly limited to, preferably 0.05-10 times (v/w) and more preferably 0.1-3 times (v/w) the amount of the compound of formula [10a] or a salt thereof.

The compound of general formula [14] is used at a molar ratio of 1 to 10 times, preferably 1 to 2 times with respect to the compound of formula [10a] or a salt thereof.

The reaction temperature is not particularly limited but is 30 to 150° C., preferably 50 to 100° C.

The reaction time is not particularly limited but is 10 minutes to 50 hours and is preferably 30 minutes to 24 hours.

The compound of general formula [1a] obtained in this manner can be used in the next reaction without isolating.

(5-2)

The compound of general formula [1a] is prepared by performing a Friedel-Crafts reaction between a reactive derivative of the compound of formula [10a] or a salt thereof and a compound of general formula [14].

Examples of the solvent used for this reaction, but not particularly limited as long as it does not affect the reaction, include halogenated hydrocarbons such as methylene chloride, chloroform, 1,2-dichloroethane, chlorobenzene and dichlorobenzene; aliphatic hydrocarbons such as hexane and cyclohexane; nitro compounds such as nitromethane and nitrobenzene; and carbon disulfide. With these solvents, one type can be used or two or more can be used in combination. Preferred solvents include nitro compounds and halogenated hydrocarbons, and nitromethane and methylene chloride are more preferred. The usage amount of the solvent is, but not particularly limited to, preferably 1-50 times (v/w), more preferably 1-15 times (v/w) the amount of the compound of formula [10a] or a salt thereof.

Regarding the reactive derivative of the compound of formula [10a] or a salt thereof used for this reaction, examples include acid halides or acid anhydrides.

The acid halide or acid anhydride of the compound of formula [10a] or a salt thereof is prepared by reacting the compound of formula [10a] or a salt thereof with an activator such as thionyl chloride, oxalyl chloride, phosphorus pentachloride, acetic anhydride, and carbonochloridic acid ethyl ester. The activator is used at a molar ratio of 1 to 10 times, preferably 1 to 3 times with respect to the compound of formula [10a] or a salt thereof. In addition, in the reaction that results in an acid halide of the compound of formula [10a] or a salt thereof, N,N-dimethylformamide is added as a catalyst at a molar ratio of 0.001-1 times, preferably 0.001-0.5 times with respect to the compound of formula [10a] or a salt thereof.

For the acid used for this reaction, examples include tin tetrachloride, aluminum chloride, trifluoroborane, and zinc chloride. The acid is used at a molar ratio of 1 to 10 times, preferably 1 to 5 times with respect to the compound of formula [10a] or a salt thereof.

The compound of general formula [14] is used at a molar ratio of 1 to 10 times, preferably 1 to 2 times with respect to the compound of formula [10a] or a salt thereof.

The reaction temperature is not particularly limited but is −78 to 100° C., preferably −50 to 70° C.

The reaction time is not particularly limited but is 10 minutes to 50 hours and is preferably 10 minutes to 24 hours.

[Preparation Method 6]

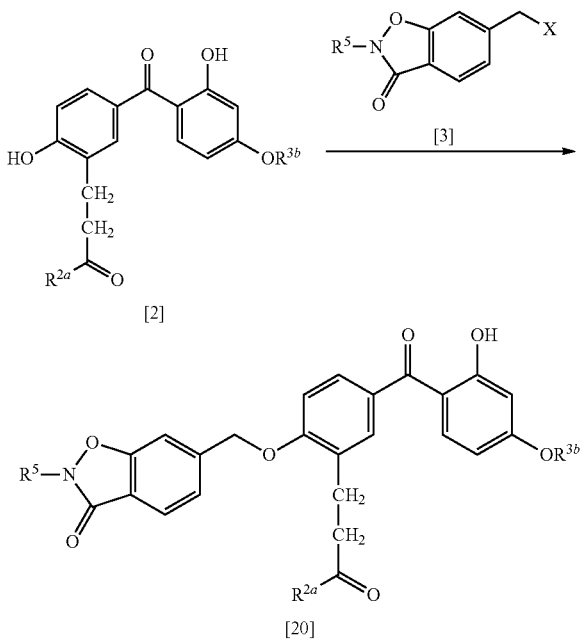

In the formula $R^{2a}$, $R^{3b}$, $R^5$ and X are as described above.

The compound of general formula [20] or a salt thereof is prepared by reacting the compound of general formula [2] or a salt thereof with the compound of general formula [3].

The compound of general formula [20] or a salt thereof is prepared by performing an alkylating reaction between the compound of general formula [2] or a salt thereof and the compound of general formula [3].

Examples of the solvent used for this reaction, but not particularly limited as long as it does not affect the reaction, include aromatic hydrocarbons such as benzene, toluene, and xylene; ethers such as dioxane, tetrahydrofuran, ethylene glycol dimethyl ether, and diethylene glycol dimethyl ether; amides such as 1-methyl-2-pyrrolidone, N,N-dimethylformamide, and N,N-dimethylacetamide; ketones such as acetone and 2-butanone; halogenated hydrocarbons such as methylene chloride, chloroform, 1,2-dichloroethane, chlorobenzene, and dichlorobenzene. These solvents can be used alone or two or more solvents can be used in combination. Preferable solvents include ketones, and acetone and 2-butanone are more preferred. The usage amount of the solvent is, but not particularly limited to, preferably 1-50 times (v/w), more preferably 1-15 times (v/w) the amount of the compound of general formula [2] or a salt thereof.

Examples of the base used for this reaction include organic bases such as dimethylaminopyridine, triethylamine, and pyridine; alkali metal hydrides such as sodium hydride; and alkali metal carbonates such as potassium carbonate and sodium carbonate. Preferable bases include alkali metal carbonates such as potassium carbonate and sodium carbonate and the like, and potassium carbonate is more preferred. The base is used at a molar ratio of 0.5-20 times, preferably 0.5-5 times with respect to the compound of general formula [2] or a salt thereof.

The compound of general formula [3] is used for this reaction at a molar ratio of 1-20 times, and preferably 1-5 times with respect to the compound of general formula [2] or a salt thereof.

The reaction temperature is not particularly limited but is 0 to 120° C., preferably 50 to 120° C.

The reaction time is not particularly limited but is 10 minutes to 50 hours and is preferably 30 minutes to 24 hours.

Next, the method for preparing the compounds of formula [5] and formula [12] or salts thereof which are used in the preparation of the present invention will be described. These compounds are prepared by combining methods that are known, but, for example, they can be prepared by the following preparation method.

[Preparation Method A]

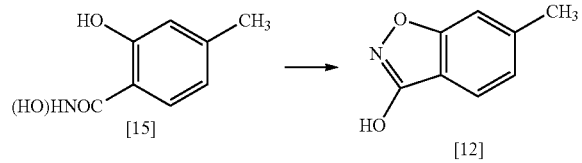

The compound of formula [15] or a salt thereof is prepared by, for example, methods described in International Publication WO03/042150 pamphlet or US patent application No. 2005/0143434.

The compound of formula [12] or a salt thereof is prepared by reacting the compound of formula [15] or a salt thereof with a thionyl halide, and then, in the presence of a base, conducting an intramolecular cyclization reaction.

For the thionyl halide used for this reaction, examples include thionyl chloride and thionyl bromide, and thionyl chloride is preferred. The thionyl halide is used at a molar ratio of 1 or greater times, preferably 1-10 times with respect to the compound of formula [15] or a salt thereof.

Examples of the base used for this reaction include organic bases such as triethylamine, N,N-diisopropylethylamine, tributylamine, pyridine, dimethylaminopyridine, N-methylmorpholine, and 1,8-diazabicyclo[5.4.0]undec-7-ene (DBU); and inorganic bases such as sodium hydroxide, potassium hydroxide, sodium carbonate, and potassium carbonate. Preferable bases are organic bases, and tributylamine is more preferred. The base is used at a molar ratio of 1 or greater times, preferably 1-5 times with respect to the compound of formula [15] or a salt thereof.

Examples of the solvent used for this reaction, but not particularly limited as long as it does not affect the reaction, include aromatic hydrocarbons such as benzene, toluene, xylene, and mesitylene; ethers such as dioxane, tetrahydrofuran, tert-butyl methyl ether, cyclopentyl methyl ether, anisole, ethylene glycol dimethyl ether, and diethylene glycol dimethyl ether; halogenated hydrocarbons such as chloroform, methylene chloride, chlorobenzene, and dichlorobenzene; and sulfolane. These can be used in combination. Preferred solvents include ethers, and tert-butyl methyl ether is more preferred. The usage amount of the solvent is, but not particularly limited to, preferably 1-50 times (v/w), more preferably 1-15 times (v/w) the amount of the compound of formula [15] or a salt thereof.

The reaction temperature is not particularly limited but is −30 to 30° C., preferably −20 to 20° C.

The reaction time is not particularly limited but is 5 minutes to 50 hours and is preferably 5 minutes to 24 hours.

The compound of formula [12] or a salt thereof obtained in this manner can be used in the next reaction without isolating, but preferably it is isolated, for example, by the usual methods such as extraction and crystallization.

[Preparation Method B]

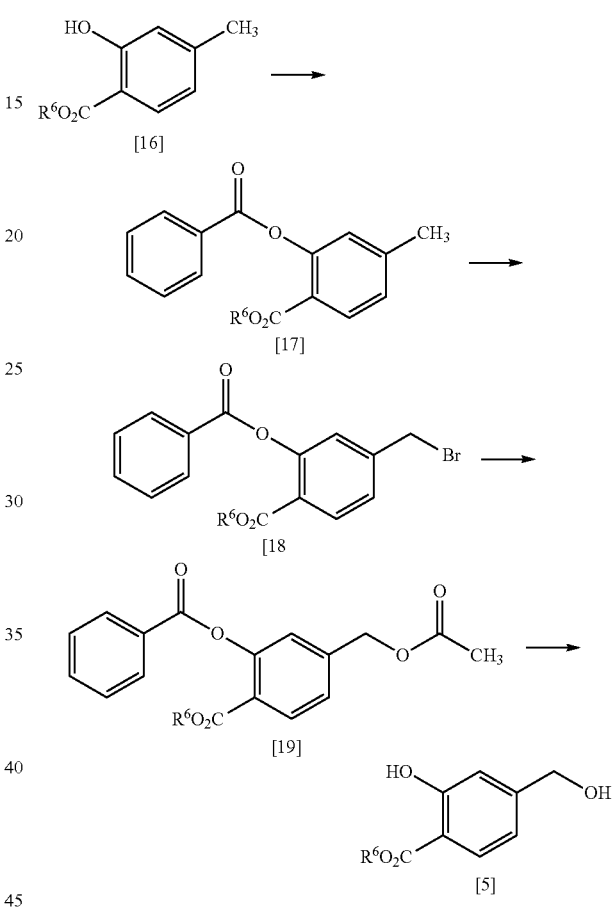

In the formula $R^6$ is as described above.

Regarding the compound of general formula [16] or a salt thereof, 2-hydroxy-4-methyl benzoic acid methyl ester is known for example.

(B-1)

The Compound of General Formula [17] can be prepared, for example, by a method described in Protective Groups In Organic Synthesis, T. W. Greene, John Wiley & Sons, Inc. 1999, third edition, p. 149-179, 276-280. Stated more concretely, it is prepared, for example, by reacting the compound of general formula [16] or a salt thereof with a benzoyl halide in the presence of a base.

Examples of the base used for this reaction include organic bases such as dimethylaminopyridine, triethylamine, pyridine, and N-methylmorpholine; and alkali metal carbonates such as potassium carbonate and sodium carbonate. Preferred bases are organic bases, and triethylamine is more preferred. The base is used at a molar ratio of 1-20 times, preferably 1-5 times with respect to the compound of general formula [16] or a salt thereof.

Regarding the benzoyl halide used for this reaction, examples include benzoyl chloride and benzoyl bromide, and benzoyl chloride is preferred. The benzoyl halide is used at a molar ratio of 1-10 times, preferably 1-3 times with respect to the compound of general formula [16] or a salt thereof.

Examples of the solvent used for this reaction, but not particularly limited as long as it does not affect the reaction, include nitriles such as acetonitrile; aromatic hydrocarbons such as benzene, toluene, xylene, and mesitylene; ethers such as dioxane, tetrahydrofuran, anisole, ethylene glycol dimethyl ether, and diethylene glycol dimethyl ether; aliphatic hydrocarbons, such as hexane and cyclohexane; halogenated hydrocarbons such as chloroform, methylene chloride, chlorobenzene, and dichlorobenzene; esters such as methyl acetate, ethyl acetate, and butyl acetate; amides such as N,N-dimethylformamide, and N,N-dimethylacetamide; and sulfoxides such as dimethyl sulfoxide. These can be used in combination. Preferable solvents include aromatic hydrocarbons, and toluene is more preferred. The usage amount of the solvent is, but not particularly limited to, preferably 1-50 times (v/w), more preferably 1-15 times (v/w) the amount of the compound of general formula [16] or a salt thereof.

The reaction temperature is not particularly limited but is −50 to 150° C., preferably −30 to 100° C.

The reaction time is not particularly limited but is 5 minutes to 50 hours and is preferably 5 minutes to 24 hours.
(B-2)

The Compound of General Formula [18] is prepared by brominating the compound of general formula [17]. This reaction is conducted according to the preparation method (2-2).
(B-3)

The Compound of General Formula [19] is prepared by, for example, reacting the compound of general formula [18] with acetate.

Regarding the acetate used for this reaction, examples include potassium acetate and sodium acetate, and potassium acetate is preferred. The acetate is used at a molar ratio of 1-10 times, preferably 1-3 times with respect to the compound of general formula [18].

In addition, the acetate can be prepared in situ.

Examples of the solvent used for this reaction, but not particularly limited as long as it does not affect the reaction, include nitriles such as acetonitrile; aromatic hydrocarbons such as benzene, toluene, xylene, and mesitylene; ethers such as dioxane, tetrahydrofuran, anisole, ethylene glycol dimethyl ether, and diethylene glycol dimethyl ether; aliphatic hydrocarbons, such as hexane and cyclohexane; halogenated hydrocarbons such as chloroform, methylene chloride, chlorobenzene, and dichlorobenzene; esters such as methyl acetate, ethyl acetate, and butyl acetate; amides such as N,N-dimethylformamide, and N,N-dimethylacetamide; and sulfoxides such as dimethyl sulfoxide. These can be used in combination. Preferable solvents include mixed solvents of esters and amides, and a mixed solvent of ethyl acetate and N,N-dimethylformamide is more preferred. The usage amount of the solvent is, but not particularly limited to, preferably 1-50 times (v/w), more preferably 1-15 times (v/w) the amount of the compound of general formula [18].

The reaction temperature is not particularly limited but is 0 to 200° C., preferably 0 to 100° C.

The reaction time is not particularly limited but is 5 minutes to 50 hours and is preferably 5 minutes to 24 hours.
(B-4)

The Compound of General Formula [5] or a Salt thereof is prepared by hydrolysis of the compound of general formula [19]. Stated more concretely, it is prepared by, for example, reacting the compound of general formula [19] with a metal alkoxide.

For the metal alkoxide used for this reaction, examples include sodium methoxide and sodium ethoxide, and sodium methoxide is preferred. When the metal alkoxide that is used is sodium methoxide, it is preferably used as a methanol solution. The metal alkoxide is used at a molar ratio of 2-10 times, preferably 2-3 times with respect to the compound of general formula [19].

Examples of the solvent used for this reaction, but not particularly limited as long as it does not affect the reaction, include nitriles such as acetonitrile; aromatic hydrocarbons such as benzene, toluene, xylene, and mesitylene; ethers such as dioxane, tetrahydrofuran, anisole, ethylene glycol dimethyl ether, and diethylene glycol dimethyl ether; aliphatic hydrocarbons such as hexane and cyclohexane; halogenated hydrocarbons such as chloroform, methylene chloride, chlorobenzene, and dichlorobenzene; alcohols such as methanol, ethanol, propanol, 2-propanol, and butanol; amides such as N,N-dimethylformamide, and N,N-dimethylacetamide; and sulfoxides such as dimethyl sulfoxide; and water. These can be used in combination. Preferable solvents include a mixed solvent of aromatic hydrocarbons and alcohols, and a mixed solvent of toluene and methanol is more preferred. The usage amount of the solvent is, but not particularly limited to, preferably 1-50 times (v/w), more preferably 1-15 times (v/w) the amount of the compound of general formula [19].

The reaction temperature is not particularly limited but is 0 to 150° C., preferably 0 to 100° C.

The reaction time is not particularly limited but is 5 minutes to 50 hours and is preferably 5 minutes to 24 hours.

The compounds obtained by the preparation methods described above can be isolated and purified by the usual methods such as extraction, crystallization, distillation, and column chromatography.

In addition, with the compounds used in the preparation methods described above, when isomers are present (for example, optical isomers, geometric isomers, and tautomers), all of these isomers can be used, and in addition metal salts, hydrates, solvates, and all crystal forms can be used.

Next, the present invention will be described citing examples and preparation examples, but the present invention is not limited to these.

For the silica gel, if not stated otherwise, B.W. Silica gel BW-127ZH (Fuji Silysia Chemical Ltd.) was used.

The mixture ratio in the eluent is a volume ratio.

For each example and preparation example, each of the abbreviations is defined as follows.
Me: methyl; THP: tetrahydropyranyl; Tr: triphenylmethyl; DMSO-$d_6$: deuterated dimethyl sulfoxide Example 1-1

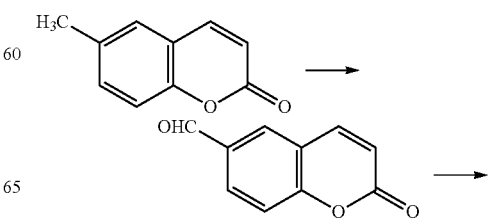

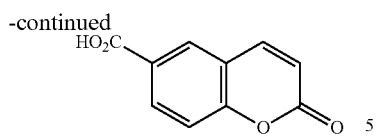

17 L of water was added dropwise into 79 L of 62.5% sulfuric acid, and after adding 13.0 kg of 6-methyl-2H-chromen-2-one and 13 L of chlorobenzene, 20.8 kg of manganese dioxide was divided into 8 parts and added at 70-90° C. A further 10 L of 62.5% sulfuric acid was added dropwise at 70-90° C., and this was stirred for 1 hour at 80-90° C. After cooling the reaction mixture, 75 L of water was added, and 22 L of 25% ammonia water was added. Next, 26 L of ethyl acetate and 52 L of 2-butanone were added, and the aqueous layer was removed. To the resulting reaction mixture, 111 L of 2-butanone and 13 L of water were added, and the organic layer was separated, and 7.8 L of dimethyl sulfoxide and 3.9 L of hydrochloric acid were added. 26 L of 25% sodium chlorite aqueous solution was added dropwise at 15-40° C., and this was stirred for 30 minutes at the same temperature. After stirring the reaction mixture at 74-80° C. for 15 minutes, the organic layer was separated. 65 L of water was added to the organic layer, and 13 L of 25% ammonia water was added dropwise at 30-40° C., and the aqueous layer was separated. 52 L of dimethyl sulfoxide was added to the aqueous layer, and 8 L of hydrochloric acid was added dropwise at 30-40° C., and after a further 8 L of hydrochloric acid was added dropwise at 65-75° C., this was stirred at the same temperature for 30 minutes. The reaction mixture was cooled, and the solid was filtered, and 9.03 kg of a pale yellow-brown solid of 2-oxo-2H-chromene-6-carboxylic acid was obtained.

$^1$H-NMR (DMSO-$d_6$) δ: 6.59 (1H, d, J=9.6 Hz), 7.49 (1H, d, J=8.6 Hz), 8.12 (1H, dd, J=8.6, 1.9 Hz), 8.20 (1H, d, J=9.6 Hz), 8.36 (1H, d, J=1.9 Hz), 13.22 (1H, brs)

Example 1-2

260 mL of water was added dropwise into 1220 mL of 62.5% sulfuric acid, and after adding 200 g of 6-methyl-2H-chromen-2-one and 200 mL of chlorobenzene, 320 g of manganese dioxide was divided into 8 parts and added at 70-90° C. A further 160 mL of 62.5% sulfuric acid was added dropwise at 70-90° C., and this was stirred for 30 minutes at 80-90° C. After cooling the reaction mixture, 1160 mL of water was added, and 340 mL of 25% ammonia water was added dropwise. Next, 400 mL of ethyl acetate and 800 mL of 2-butanone were added, and the aqueous layer was removed. To the resulting reaction mixture, 1700 mL of 2-butanone and 200 mL of water were added, and the organic layer was separated, and 120 mL of dimethyl sulfoxide and 800 mL of water were added. 80 mL of 25% ammonia water was added dropwise. 360 mL of 25% sodium chlorite aqueous solution was added dropwise at 25-40° C., and this was stirred for 1 hour at the same temperature. Next, 108 mL of 25% ammonia water was added dropwise into the reaction mixture at 25-35° C., and the aqueous layer was separated. 600 mL of methanol was added to the aqueous layer, and 40 mL of hydrochloric acid was added dropwise. Next, 15.7 g of sodium sulfite was added in two parts at 25-30° C., and this was stirred for 30 minutes. After dropping a further 200 mL of hydrochloric acid at 40-50° C., the reaction mixture was cooled, and the solid was filtered and collected, and 144 g of a pale yellow-brown solid of 2-oxo-2H-chromene-6-carboxylic acid was obtained.

The $^1$H-NMR in the DMSO-$d_6$ was the same as the values of Examples 1-1.

Example 2

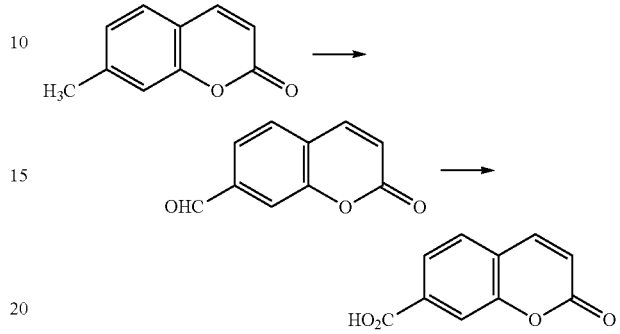

7 mL of water was added dropwise into 31 mL of 62.5% sulfuric acid, and after adding 5.00 g of 7-methyl-2H-chromen-2-one and 5 mL of chlorobenzene, 8.00 g of manganese dioxide was divided into 8 parts and added at 70-90° C. A further 4 mL of 62.5% sulfuric acid was added dropwise at 70-90° C., and this was stirred for 1 hour at 80-90° C. After cooling the reaction mixture, 29 mL of water was added, and 9 mL of 25% ammonia water was added dropwise. Next, 10 mL of ethyl acetate and 20 mL of 2-butanone were added, and the aqueous layer was removed. To the resulting reaction mixture, 43 mL of 2-butanone and 5 mL of water were added, and the organic layer was separated, and 3 mL of dimethyl sulfoxide and 2 mL of hydrochloric acid were added. 10 mL of 25% sodium chlorite aqueous solution was added dropwise at 15-40° C., and this was stirred for 30 minutes at the same temperature. The reaction mixture was stirred at 74-80° C., and the organic layer was separated. 40 mL of water and 15 mL of 2-butanone were added to the organic layer. 5 mL of 25% ammonia water was added dropwise at 30-40° C., and the aqueous layer was separated. 30 mL of dimethyl sulfoxide was added to the aqueous layer, and 3 mL of hydrochloric acid was added dropwise at 30-40° C. After dropping a further 5 mL of hydrochloric acid at 65-75° C., this was stirred for 30 minutes at the same temperature. The reaction mixture was cooled, and the solid was filtered and collected, and 1.67 g of a pale yellow-brown solid of 2-oxo-2H-chromene-7-carboxylic acid was obtained.

$^1$H-NMR (DMSO-$d_6$) δ: 6.63 (1H, d, J=9.5 Hz), 7.80-7.90 (3H, m), 8.14 (1H, d, J=9.5 Hz)

Example 3

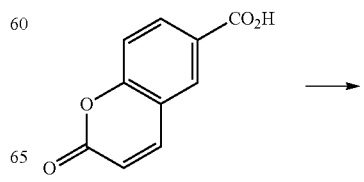

-continued

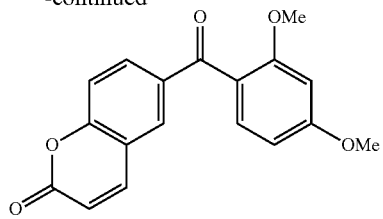

6.85 kg of diphosphorus pentoxide was added to 46 L of methanesulfonic acid, and after stirring for 1 hour at 70-80° C., 17.0 kg of 2-oxo-2H-chromene-6-carboxylic acid and 1.7 L of chlorobenzene were added, and 13.0 kg of 1,3-dimethoxybenzene was added dropwise at 70-80° C., and this was stirred for 3 hours at the same temperature. After cooling the reaction mixture, 94 L of 2-butanone was added, and 34 L of water and then 55 L of 25% ammonia water were added dropwise. Next, the reaction mixture was heated to 65-75° C., and the organic layer was separated. 26 L of 2-butanone and 34 L of water were added to the organic layer, and 2.6 L of 25% ammonia water was added dropwise. The reaction mixture was heated to 65-75° C., and the organic layer was separated. The organic layer was heated, and 77 L of solvent was distilled off under atmospheric pressure. 17 L of 4-methyl-2-pentanone was added to the reaction mixture, and 60 L of methanol and then 120 L of water were added dropwise at 40-65° C. After stirring the reaction mixture for 30 minutes at 10-25° C., the solid was filtered and collected, and 19.0 kg of a pale yellow-brown solid of 6-(2,4-dimethoxybenzoyl)-2H-chromen-2-one was obtained.

$^1$H-NMR (CDCl$_3$) δ: 3.69 (3H, s), 3.89 (3H, s), 6.47 (1H, d, J=9.8 Hz), 6.52 (1H, d, J=2.2 Hz), 6.59 (1H, dd, J=8.5, 2.2 Hz), 7.35 (1H, d, J=8.5 Hz), 7.45 (1H, d, J=8.5 Hz), 7.74 (1H, d, J=9.8 Hz), 7.91 (1H, dd, J=8.5, 2.0 Hz), 7.95 (1H, d, J=2.0 Hz)

Example 4

478 g of 6-(2,4-dimethoxybenzoyl)-2H-chromen-2-one was added to a mixture solution of 480 mL of pyridine, 240 mL of 1-methyl-2-pyrrolidone and 480 mL of toluene. Next, 454 mL of hydrochloric acid was added dropwise. The reaction mixture was heated, and while conducting azeotropic dehydration, this was stirred for 2 hours at 200-210° C. After cooling the reaction mixture to 85-110° C., 480 mL of N,N-dimethylformamide was added, 2.4 L of water was added dropwise at 85-95° C. After stirring the reaction mixture for 30 minutes at 10-25° C., the solid was filtered and collected. 421 g of a pale yellow-brown solid of 6-(2,4-dihydroxybenzoyl)-2H-chromen-2-one was obtained.

$^1$H-NMR (DMSO-d$_6$) δ: 6.38-6.42 (2H, m), 6.60 (1H, d, J=9.5 Hz), 7.41 (1H, d, J=8.8 Hz), 7.53 (1H, d, J=8.5 Hz), 7.86-7.88 (1H, m), 8.06 (1H, d, J=2.0 Hz), 8.18 (1H, d, J=9.5 Hz), 10.69 (1H, s), 11.82 (1H, s)

Example 5-1

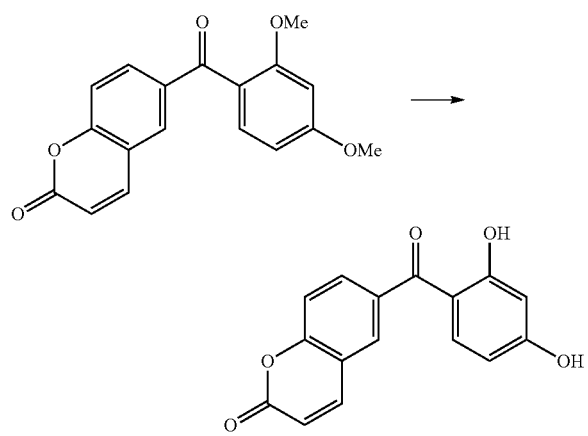

9.25 kg of potassium carbonate, 21.0 kg of 6-(2,4-dihydroxybenzoyl)-2H-chromen-2-one and 16.6 kg of cyclopentyl bromide were added to 63 L of N,N-dimethylformamide, and this was stirred for 2 hours at 90-100° C. After cooling the reaction mixture, 63 L of toluene, 21 L of 2-butanone and 84 L of water were added. Next, 1.26 kg of potassium carbonate was added, and the organic layer was separated. After adding 11 L of methanol and 21 L of toluene to the organic layer, 63 L of solvent was distilled off under atmospheric pressure. 33.0 kg of 28% sodium methoxide/methanol solution was added dropwise into the resulting reaction mixture at 55-65° C. This was stirred for 1 hour at the same temperature. The reaction mixture was cooled, and after sequentially adding 16 L of hydrochloric acid and 32 L of toluene, 63 L of water was added dropwise at 60-70° C. The organic layer was separated, and after adding 21 L of toluene, 42 L of solvent was distilled off under atmospheric pressure. After stirring the reaction mixture for 30 minutes at 75-85° C., 42 L of cyclohexane and 42 L of water were added dropwise at 10-25° C. After stirring for 30 minutes at the same temperature, the solid was filtered and collected, and 20.3 kg of a pale yellow-brown solid of (E)-3-{5-[4-cyclopentyloxy)-2-hydroxybenzoyl]-2-hydroxyphenyl} acrylic acid methyl ester was obtained.

$^1$H-NMR (DMSO-d$_6$) δ: 1.50-1.80 (6H, m), 1.90-2.00 (2H, m), 3.72 (3H, s), 4.85-4.95 (1H, m), 6.48-6.50 (2H, m), 6.68 (1H, d, J=16.1 Hz), 7.05 (1H, d, J=8.5 Hz), 7.44-7.47 (1H, m), 7.59-7.61 (1H, m), 7.86 (1H, d, J=16.1 Hz), 7.92 (1H, d, J=2.2 Hz), 11.20 (1H, brs), 11.94 (1H, s)

Example 5-2

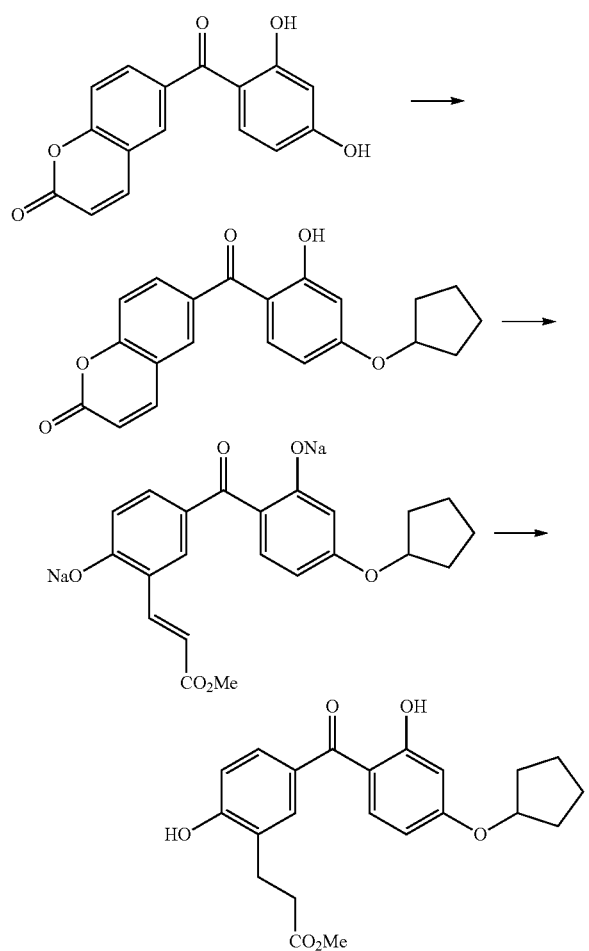

8.81 g of potassium carbonate, 20.0 g of 6-(2,4-dihydroxybenzoyl)-2H-chromen-2-one and 15.8 g of cyclopentyl bromide were added to 60 mL of N,N-dimethylformamide, and this was stirred for 2.5 hours at 90-100° C. After cooling the reaction mixture, 60 mL of toluene and 80 mL of water were added. Next, 2.40 g of potassium carbonate was added, and the organic layer was separated. After adding 10 mL of methanol and 30 mL of toluene to the organic layer, 60 mL of solvent was distilled off under atmospheric pressure. 31.4 g of 28% sodium methoxide/methanol solution was added dropwise at 55-65° C. into the resulting reaction mixture. After stirring for 1 hour at the same temperature, 10 mL of the solvent was distilled off under atmospheric pressure. The reaction mixture was cooled, and 100 mL of 2-butanone was added dropwise at 10-25° C. After stirring for 30 minutes at the same temperature, the solid was filtered and collected. Next, this solid was added to a mixture solution of 80 mL of 2-propanol, 5.44 g of formic acid, 7.23 g of acetic acid and 16 mL of water. In addition, a suspension of 1.50 g of 10% palladium on carbon in 10 mL of water was added, and this was stirred for 3 hours at 40-45° C. After cooling the reaction mixture to 25-35° C., 1.0 g of celite was added, and after stirring for 5 minutes at the same temperature, the insoluble matter was filtered off. The cake was washed with a mixture solution of 20 mL of 2-propanol and 14 mL of water. The filtrate and washing solution were mixed, and after adding 30 mL of water and 20 mg of 3-{5-[4-(cyclopentyloxy)-2-hydroxybenzoyl]-2-hydroxyphenyl}propionic acid methyl ester, this was stirred for 1 hour at 10-20° C. 100 mL of water was added dropwise at 10-25° C. to the reaction mixture, and after stirring for 30 minutes at 10-20° C., the solid was filtered, and 15.7 g of a pale yellow-brown solid of 3-{5-[4-(cyclopentyloxy)-2-hydroxybenzoyl]-2-hydroxyphenyl}propionic acid methyl ester was obtained.

The $^1$H-NMR in DMSO-$d_6$ was identical to the values of Examples 8.

Example 6

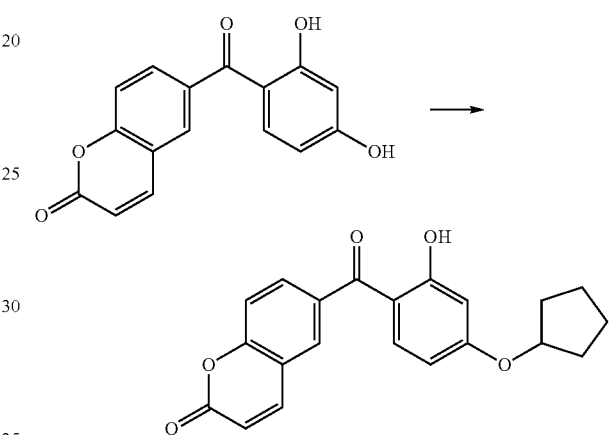

13.3 mL of cyclopentyl bromide and 17.1 g of potassium carbonate were added to 75 mL of N,N-dimethylformamide solution of 25.0 g of 6-(2,4-dihydroxybenzoyl)-2H-chromen-2-one. This was stirred for 4 hours at 78-82° C. After cooling the reaction mixture, 125 mL of water and 50 mL of toluene were added, and this was heated to 40-50° C., and the organic layer was separated. After adding 125 mL of 2-propanol to the organic layer, the solid was heated and dissolved. After stirring the reaction mixture for 30 minutes at 40-45° C. and for 1 hour at 10° C., the solid was filtered and collected and 22.8 g of a pale yellow-brown solid of 6-[4-(cyclopentyloxy)-2-hydroxybenzoyl]-2H-chromen-2-one was obtained.

$^1$H-NMR (DMSO-$d_6$) δ: 1.55-1.80 (6H, m), 1.90-2.05 (2H, m), 4.85-5.00 (1H, m), 6.50-6.53 (2H, m), 6.59 (1H, d, J=9.5 Hz), 7.45 (1H, d, J=8.8 Hz), 7.54 (1H, d, J=8.5 Hz), 7.87-7.90 (1H, m), 8.08 (1H, d, J=2.2), 8.18 (1H, d, J=9.5), 11.67 (1H, brs)

Example 7

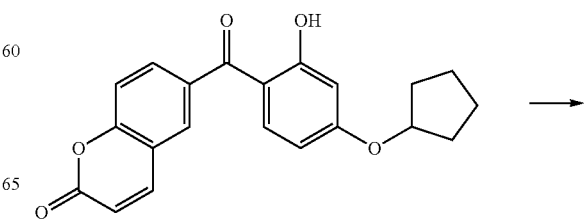

-continued

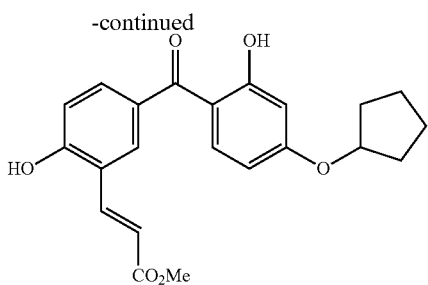

33.0 g of 28% sodium methoxide/methanol solution was added to a suspension of 30.0 g of 6-[4-(cyclopentyloxy)-2-hydroxybenzoyl]-2H-chromen-2-one in 60 mL of toluene and 60 mL of methanol. This was heated under reflux for 3 hours. After ice-cooling the reaction mixture, 90 mL of water was added, and this was adjusted to pH 1.2 with hydrochloric acid. Next, 90 mL of ethyl acetate was added, and the organic layer was separated. After adding 30 mL of ethyl acetate to the organic layer, 140 mL of solvent was distilled off under atmospheric pressure. 90 mL of cyclohexane was added dropwise at 70-75° C. into the reaction mixture. After stirring this for 30 minutes at 65-70° C. and for 1 hour at 10° C., the solid was filtered and collected, and 24.2 g of a pale yellow-brown solid of (E)-3-{5-[4-(cyclopentyloxy)-2-hydroxybenzoyl]-2-hydroxyphenyl} acrylic acid methyl ester was obtained.

The $^1$H-NMR in DMSO-$d_6$ was identical to the values of Examples 5-1.

Example 8

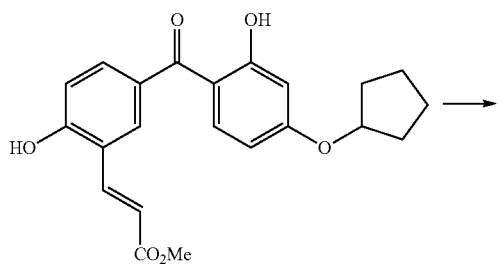

20.5 kg of (E)-3-{5-[4-(cyclopentyloxy)-2-hydroxybenzoyl]-2-hydroxyphenyl} acrylic acid methyl ester, 5.47 kg of acetic acid and 5.47 kg of sodium formate were added to 62 L of 2-propanol. A suspension of 3.08 kg of 5% palladium on carbon in 21 L of water was added, and this was stirred for 7 hours at 40-45° C. After cooling the reaction mixture to 25-35° C., 2 kg of celite was added. After stirring for 5 minutes at the same temperature, the insoluble matter was filtered off, and the cake was washed with a mixture solution of 41 L of 2-propanol and 20 L of water. The filtrate and the washing solution were mixed, and the organic layer was separated. After adding 31 L of water to the organic layer, this was stirred for 1 hour at 10-20° C. 82 L of water was added dropwise at 10-25° C. into the reaction mixture, and after stirring for 1 hour at 10-20° C., the solid was filtered and collected, and 18.0 kg of a pale yellow-brown solid of 3-{5-[4-(cyclopentyloxy)-2-hydroxybenzoyl]-2-hydroxyphenyl}propionic acid methyl ester was obtained.

$^1$H-NMR (DMSO-$d_6$) δ: 1.50-1.80 (6H, m), 1.85-2.00 (2H, m), 2.61 (2H, t, J=7.6 Hz), 2.83 (2H, t, J=7.6 Hz), 3.58 (3H, s), 4.85-4.95 (1H, m), 6.45-6.49 (2H, m), 6.92 (1H, d, J=8.3 Hz), 7.42-7.47 (3H, m), 10.40 (1H, brs), 12.07 (1H, s)

Example 9

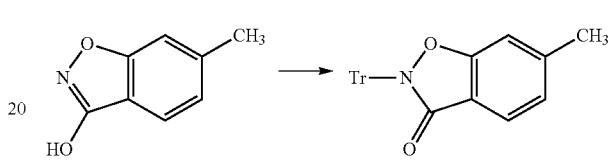

20.0 g of 6-methyl-1,2-benzisoxazol-3-ol, 9.93 g of pyridine and 35.0 g of triphenylmethyl chloride were added to 100 mL of methylene chloride, and this was stirred for 1 hour at 35-45° C. 40 mL of water and 24 mL of 20% sodium hydroxide aqueous solution were added to the reaction mixture, and the organic layer was separated. The aqueous layer was extracted with 20 mL of methylene chloride, and the organic layers were combined, and 70 mL of the solvent was distilled off under atmospheric pressure, and 100 mL of 2-propanol was added, and 40 mL of the solvent was distilled off under atmospheric pressure. 40 mL of water was added to the reaction mixture, and after stirring for 30 minutes at 10-25° C., the solid was filtered and collected, and 46.0 g of a pale yellow solid of 6-methyl-2-triphenylmethyl-1,2-benzisoxazol-3 (2H)-one was obtained.

$^1$H-NMR (DMSO-$d_6$) δ: 2.36 (3H, s), 7.03 (1H, d, J=8.0 Hz), 7.18-7.33 (10H, m), 7.43-7.47 (7H, m)

Example 10

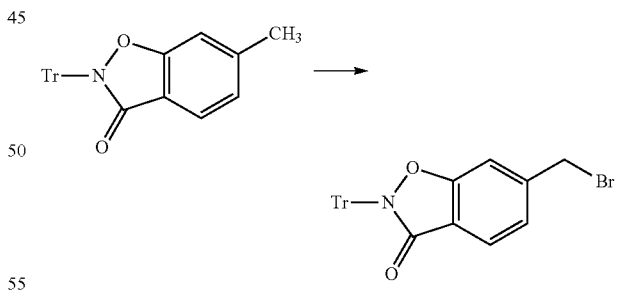

24.0 kg of 6-methyl-2-triphenylmethyl-1,2-benzisoxazol-3(2H)-one and 18.6 kg of N-bromosuccinimide were added to 48 L of chlorobenzene. A solution of 0.30 kg of 2,2'-azobis (2,4-dimethylvaleronitrile) in 4.8 L of methylene chloride was added dropwise 5 times every 1 hour at 70-80° C. After completing the instillation, this was stirred for 1 hour at the same temperature. 96 L of methylene chloride, 2.40 kg of celite, 24 L of 20% sodium hydroxide aqueous solution, 0.77 kg of sodium sulfite and 48 L of water were added to the reaction mixture. The insoluble matter was filtered off, and the cake was washed with 72 L of methylene chloride. The filtrate and washing solution were combined, and the organic layer was separated. 24 L of methylene chloride, 12.7 kg of potassium carbonate and 6.07 kg of phosphonic acid dimethyl ester were added to the organic layer, and this was stirred for 4 hours at 40-50° C. 48 L of water and 14 L of 20% sodium hydroxide aqueous solution were added to the reaction mixture, and the organic layer was separated. The aqueous layer was extracted with 24 L of methylene chloride, and the organic layers were combined, and 24 L of methylene chloride was added, and 210 L of the solvent was distilled off under atmospheric pressure. 24 L of acetone was added to the reaction mixture, and 40 L of the solvent was distilled off under atmospheric pressure. 96 L of 2-propanol and 24 L of water was added dropwise, and the solid was filtered and collected, and 25.2 kg of a white solid of 6-(bromomethyl)-2-triphenylmethyl-1,2-benzisoxazol-3(2H)-one was obtained.

$^1$H-NMR (DMSO-d$_6$) δ: 4.72 (2H, s), 7.22-7.49 (17H, m), 7.58 (1H, d, J=8.0 Hz)

Example 11

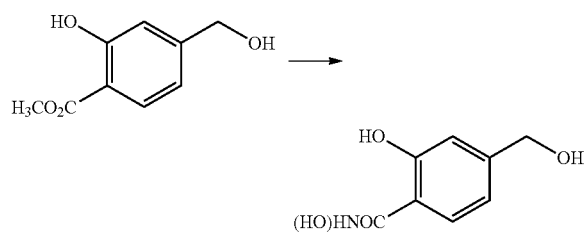

350 g of 2-hydroxy-4-(hydroxymethyl)benzoic acid methyl ester and 160 g of hydroxylamine hydrochloride were added to 700 mL of methanol. Under heating reflux, 1.11 kg of 28% sodium methoxide/methanol solution was added dropwise, and this was stirred for 3 hours. To this, 2.1 L of water was added and 850 mL of solvent was distilled off under atmospheric pressure. Then, 196 mL of hydrochloric acid was added at 40-50° C. The result was stirred for 30 minutes at the same temperature, and 116 mL of hydrochloric acid was added dropwise. After filtering solids, 291 g of N,2-dihydroxy-4-(hydroxymethyl)benzamide was obtained in the form of a pale yellowish-white solid.

$^1$H-NMR (DMSO-d$_6$) δ: 4.46 (2H, d, J=5.8 Hz), 5.26 (1H, t, J=5.8 Hz), 6.78 (1H, d, J=8.2 Hz), 6.85 (1H, s), 7.62 (1H, d, J=8.2 Hz), 9.28 (1H, s), 11.39 (1H, s), 12.25 (1H, s)

Example 12

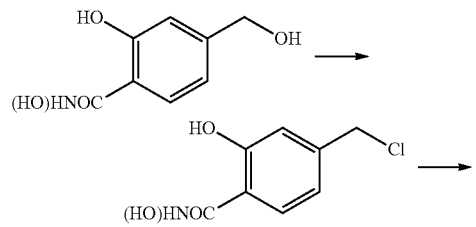

In 50 mL of methylene chloride was suspended 10.0 g of N,2-dihydroxy-4-(hydroxymethyl)benzamide. To this, 0.21 mL of N,N-dimethylformamide was added. This was cooled and 8.36 mL of thionyl chloride was added dropwise under ice-cooling. After 2 hours of stirring under heating reflux, 13 mL of solvent was distilled off under atmospheric pressure. To the reaction mixture was added 13 mL of methylene chloride, 4.64 mL of pyridine was added dropwise at 20-30° C., and the results were stirred for 1 hour at the same temperature. After adding 20 mL of water and 50 mL of acetone, 50 mL of solvent was distilled off under atmospheric pressure, solids were filtered, and 6.45 g of 6-(chloromethyl)-1,2-benzisoxazol-3-ol in the form of a pale yellowish-white solid was obtained.

$^1$H-NMR (DMSO-d$_6$) δ: 4.91 (2H, s), 7.39 (1H, dd, J=8.1, 1.1 Hz), 7.65 (1H, s), 7.76 (1H, d, J=8.1 Hz), 12.41 (1H, s)

Example 13

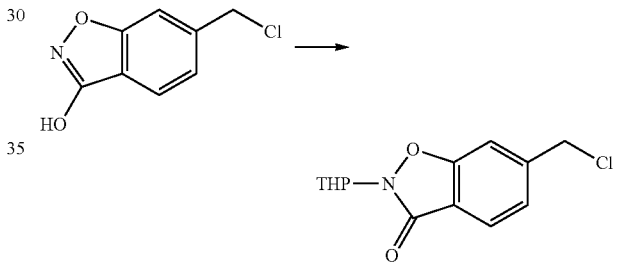

(1) In 20 mL of methylene chloride was suspended 1.00 g of 6-(chloromethyl)-1,2-benzisoxazol-3-01, and to this was added 27.0 mg of pyridinium p-toluenesulfonate and 0.596 mL of 3,4-dihydro-2H-pyran. This was stirred for 24 hours at room temperature. Solvent was distilled off under reduced pressure, and the obtained residue was purified by silica gel column chromatography (eluent; hexane:ethyl acetate=3:1). As a result, 1.10 g of 6-(chloromethyl)-2-(tetrahydro-2H-pyran-2-yl)-1,2-benzisoxazol-3(2H)-one in the form of a white solid. This served as a seed crystal.

(2) In 75 mL of methylene chloride, 5.00 g of 6-(chloromethyl)-1,2-benzisoxazol-3-ol was suspended, and to this was added 0.137 g of pyridinium p-toluenesulfonic acid and 2.98 mL of 3,4-dihydro-2H-pyran. This was stirred for 8 hours at room temperature. To the reaction mixture was added 30 mL of water and an organic layer was separated. An aqueous layer was extracted with 10 mL of methylene chloride, and this along with the organic layer was washed with an aqueous saturated sodium chloride solution and dried with anhydrous sodium sulfate. Solvent was distilled off under reduced pressure, and 20 mL of diisopropyl ether was added to the obtained residue. A seed crystal was added and, after 30 minutes of stirring at room temperature, solids were filtered to obtain 6.65 g of 6-(chloromethyl)-2-(tetrahydro-2H-pyran-2-yl)-1,2-benzisoxazol-3(2H)-one in the form of a pale yellowish-white solid.

$^1$H-NMR (DMSO-$d_6$) δ: 1.45-1.55 (2H, m), 1.62-1.77 (1H, m), 1.85-2.00 (2H, m), 2.00-2.15 (1H, m), 3.57-3.64 (1H, m), 3.89-3.93 (1H, m), 4.89 (2H, s), 5.47-5.50 (1H, m), 7.42 (1H, d, J=8.0 Hz), 7.62 (1H, s), 7.83 (1H, d, J=8.0 Hz)

Example 14

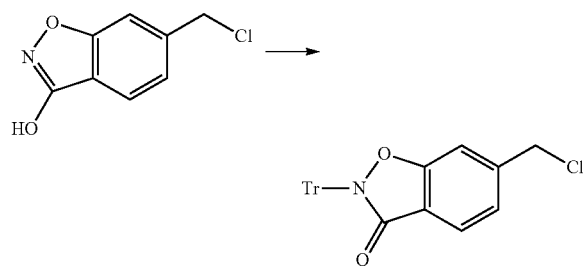

In 50 mL of methylene chloride, 5.00 g of 6-(chloromethyl)-1,2-benzisoxazol-3-ol, 7.59 g of triphenylmethyl chloride and 2.20 mL of pyridine were suspended and stirred for 5 hours at room temperature. To the reaction mixture, 15 mL of water and 15 mL of methylene chloride were added, and the result was stirred for 5 minutes under reflux and heating. After cooling the reaction mixture, 2.50 g of silica gel was added. After insoluble matter was filtered off, the cake was washed with 10 mL of methylene chloride. The filtrate and the washing solution were combined and, after adding 8 mL of methylene chloride and 15 mL of water, 45 mL of solvent was distilled off under atmospheric pressure. To the reaction mixture, 35 mL of acetone was added and 33 mL of solvent was distilled off under atmospheric pressure. After adding 20 mL of water, solids were filtered and 11.3 g of 6-(chloromethyl)-2-triphenylmethyl-1,2-benzisoxazol-3(2H)-one was obtained in the form of a pale yellowish-white solid.

$^1$H-NMR (DMSO-$d_6$) δ: 4.79 (2H, s), 7.19-7.50 (17H, m), 7.60 (1H, d, J=8.0 Hz)

Example 15

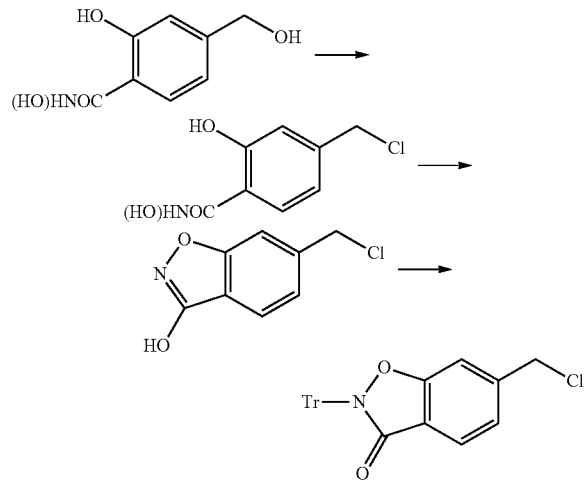

10.5 kg of N,2-dihydroxy-4-(hydroxymethyl)benzamide and 0.10 kg of N,N-dimethylformamide were added to 105 L of methylene chloride. To this, 14.3 kg of thionyl chloride was added dropwise under heating reflux, and then the result was stirred for 6 hours at the same temperature. Then, 11 L of solvent was distilled off under atmospheric pressure and, at 20-30° C., 24 L of methylene chloride and 13.6 kg of triphenylmethyl chloride were added. To this, 4.31 kg of pyridine was added dropwise and stirred for 4 hours at the same temperature. To the reaction mixture, 21 L of water was added, and an organic layer was separated. An aqueous layer was extracted with 11 L of methylene chloride. To this, along with the organic layer were added 21 L of water and 2.10 kg of celite. Then, at 20-30° C., 12.6 L of a 20% sodium hydroxide aqueous solution was added dropwise. After insoluble matter was filtered off, the cake was washed with 21 L of methylene chloride. The filtrate and the washing solution were combined and 57 L of solvent was distilled off under atmospheric pressure. To the reaction mixture was added 53 L of 2-propanol, and 53 L of solvent was distilled off under atmospheric pressure. To the reaction mixture was added 53 L of 2-propanol. After 46 L of solvent was distilled off under atmospheric pressure, the result was stirred for 30 minutes at 15-20° C. Solids were then filtered to obtain 17.6 kg of 6-(chloromethyl)-2-triphenylmethyl-1,2-benzisoxazol-3(2H)-one in the form of a pale yellowish-white solid.

The $^1$H-NMR in DMSO-$d_6$ matched the value from Example 14.

Example 16

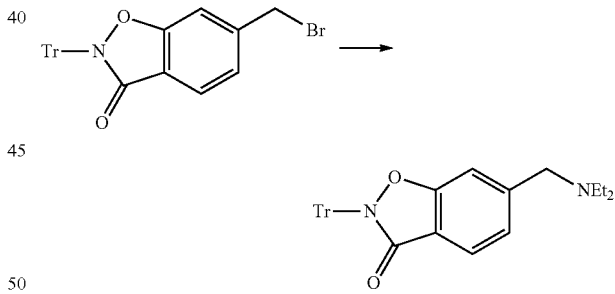

30.0 g of 6-(bromomethyl)-2-triphenylmethyl-1,2-benzisoxazol-3(2H)-one and 13.9 mL of diethylamine were added to 90 mL of N,N-dimethylformamide. This was stirred for 50 minutes at room temperature. Ethyl acetate, methylene chloride and water were added to the reaction mixture, and an organic layer was separated. Water and hydrochloric acid were added to the organic layer, and an aqueous layer was separated. An organic layer was extracted with water and, together with the aqueous layer, 180 mL of acetone was added and 13 mL of a 20% sodium hydroxide aqueous solution was added dropwise. Solids were filtered to obtain 22.2 g of 6-(diethylamino)methyl-2-triphenylmethyl-1,2-benzisoxazol-3(2H)-one was obtained in the form of a pale yellowish-white solid.

$^1$H-NMR (DMSO-d$_6$) δ: 0.94 (6H, t, J=7.1 Hz), 2.42 (4H, q, J=7.1 Hz), 3.56 (2H, s), 7.18-7.34 (11H, m), 7.45-7.51 (7H, s)

Example 17

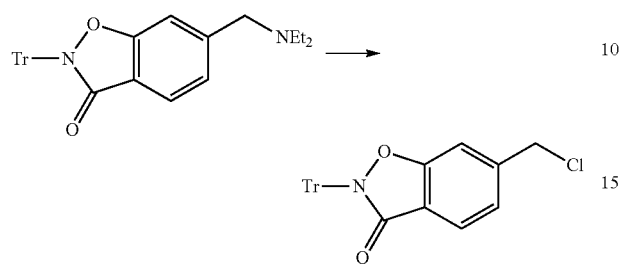

20.0 g of 6-(diethylamino)methyl-2-triphenylmethyl-1,2-benzisoxazol-3(2H)-one and 5.1 mL of ethyl chlorocarbonate were added to 60 mL of methylene chloride. This was then stirred for 3 hours at room temperature, and 140 mL of 2-propanol was added dropwise into the reaction mixture over a period of 30 minutes. The result was stirred for 2 hours at 5-15° C. and solids were filtered to obtain 16.6 g of 6-(chloromethyl)-2-triphenylmethyl-1,2-benzisoxazol-3(2H)-one in the form of a pale yellowish-white solid.

$^1$H-NMR (DMSO-d$_6$) δ: 4.80 (2H, s), 7.18-7.50 (17H, m), 7.60 (1H, d, J=8.0 Hz)

Example 18

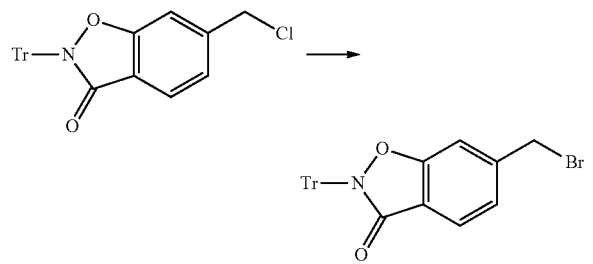

10.0 g of 6-(chloromethyl)-2-triphenylmethyl-1,2-benzisoxazol-3(2H)-one, 35 mL of bromoethane and 2.42 g of sodium bromide were added to 80 mL of N-methyl-2-pyrrolidone, and this was stirred for 1.5 hours at 55-60° C. After cooling the reaction mixture, 20 mL of 2-propanol and 50 mL of water were added dropwise and solids were filtered to obtain a white solid. The obtained white solid, 35 mL of bromoethane and 2.42 g of sodium bromide were added to 80 mL of N-methyl-2-pyrrolidone, and this was stirred for 1 hour at 55-60° C. After cooling the reaction mixture, 20 mL of 2-propanol and 50 mL of water were added dropwise and solids were filtered to obtain 9.04 g of 6-(bromomethyl)-2-triphenylmethyl-1,2-benzisoxazol-3(2H)-one in the form of a white solid.

$^1$H-NMR (DMSO-d$_6$) δ: 4.72 (2H, s), 7.20-7.51 (17H, m), 7.58 (1H, d, J=8.0 Hz)

Example 19

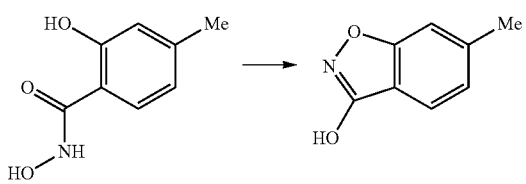

50.0 g of N,2-dihydroxy-4-methylbenzamide was added to 350 mL of tert-butylmethylether, and 38.1 g of thionyl chloride was added dropwise at −1-0° C. This was stirred for 30 minutes at the same temperature. Then, 164 mL of tributylamine was added dropwise at −5−−3° C., and this was stirred for 1.5 hours at −5-5° C. To the reaction mixture, 200 mL of 20% sodium hydroxide aqueous solution was added, an organic layer was separated, and 100 mL of water, 42 mL of 20% sodium hydroxide aqueous solution and 5.0 g of celite were added. After insoluble matter was filtered off, the cake was washed with 100 mL of water. The filtrate and the washing solution were combined and an aqueous layer was separated. To the aqueous layer, 10 mL of acetone and 50 mL of acetic acid were added at 40-50° C. After stirring at the same temperature for 30 minutes, solids were filtered to obtain 40.1 g of 6-methyl-1,2-benzisoxazol-3-ol in the form of a pale yellow solid.

$^1$H-NMR (CDCL$_3$) δ: 2.51 (3H, s), 7.13 (1H, d, J=8.0 Hz), 7.21 (1H, s), 7.65 (1H, d, J=8.0 Hz)

Example 20

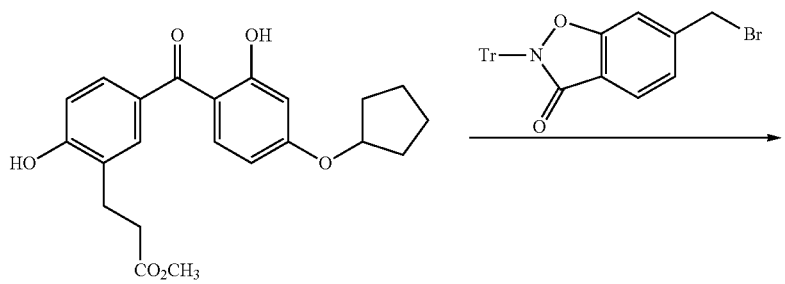

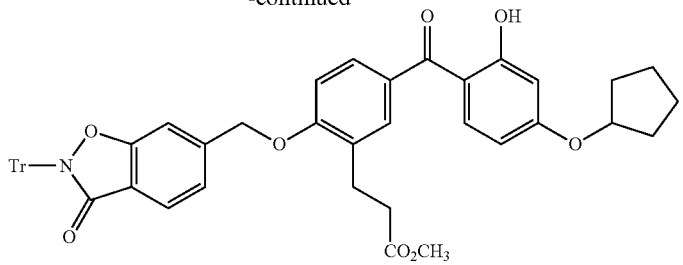

12.5 kg of 3-{5-[4-(cyclopentyloxy)-2-hydroxybenzoyl]-2-hydroxyphenyl}propionic acid methyl ester, 15.6 kg of 6-(bromomethyl)-2-triphenylmethyl-1,2-benzisoxazol-3(2H)-one and 4.49 kg of potassium carbonate were added to 125 L of acetone. This was stirred for 5 hours under heating reflux. After cooling the reaction mixture, 29 L of water was added, 2.9 L of hydrochloric acid was added dropwise, and solids were filtered. This resulted in 19.7 kg of 3-{5-[4-(cyclopentyloxy)-2-hydroxybenzoyl]-2-[(3-oxo-2-triphenylmethyl-2,3-dihydro-1,2-benzisoxazol-6-yl)methoxy]phenyl}propionic acid methyl ester in the form of a pale yellowish-white solid.

$^1$H-NMR (DMSO-$d_6$) δ: 1.55-1.78 (6H, m), 1.90-2.00 (2H, m), 2.63 (2H, t, J=7.6 Hz), 2.93 (2H, t, J=7.6 Hz), 3.49 (3H, s), 4.88-4.94 (1H, m), 5.33 (2H, s), 6.46-6.51 (2H, m), 7.13 (1H, d, J=8.3 Hz), 7.22-7.25 (3H, m), 7.30-7.34 (7H, m), 7.42-7.56 (10H, m), 7.63 (1H, d, J=8.0 Hz), 12.00 (1H, s)

Preparation Example 1

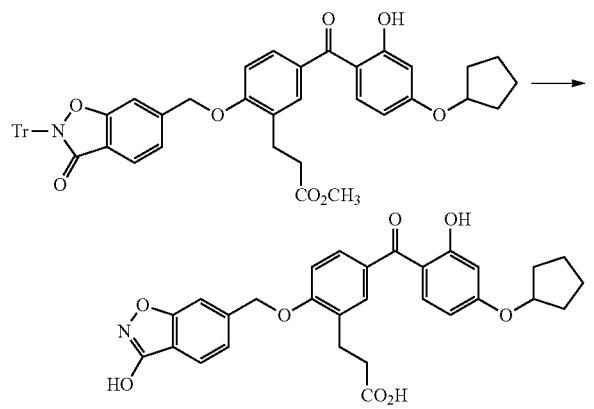

(1) 300 g of 3-{5-[4-(cyclopentyloxy)-2-hydroxybenzoyl]-2-[(3-oxo-2-triphenylmethyl-2,3-dihydro-1,2-benzisoxazol-6-yl)methoxy]phenyl}propionic acid methyl ester was added to a mixture of 1200 mL of methyl isobutyl ketone and 600 mL of methanol. 43.5 mL of sulfuric acid was added dropwise under ice-cooling. This was stirred for 1 hour under water-cooled, and then stirred for 1 hour 30 minutes at room temperature. After adding 1200 mL of water and 200 mL of 20% sodium hydroxide aqueous solution, the result was stirred at room temperature for 30 minutes and solids were filtered to obtain 167 g of 3-{5-[4-(cyclopentyloxy)-2-hydroxybenzoyl]-2-[(3-hydroxy-1,2-benzisoxazol-6-yl)methoxy]phenyl}propionic acid methyl ester in the form of a pale yellowish-white solid.

(2) In 182 mL of methanol, 26.0 g of 3-{5-[4-(cyclopentyloxy)-2-hydroxybenzoyl]-2-[(3-hydroxy-1,2-benzisoxazol-6-yl)methoxy]phenyl}propionic acid methyl ester was suspended. After dropping 78 mL of water of 10.5 g of sodium hydroxide at room temperature, the result was stirred for 30 minutes at the same temperature. The reaction mixture was added to water. After adjusting to pH 1.5 with a 6 mol/L hydrochloric acid, solids were filtered. The obtained solids were dissolved in a mixture solution of chloroform and methanol. After washing with water, solvent was distilled off under reduced pressure to obtain 22.5 g of 3-{5-[4-(cyclopentyloxy)-2-hydroxybenzoyl]-2-[(3-hydroxy-1,2-benzisoxazol-6-yl)methoxy]phenyl}propionic acid in the form of a light yellowish solid.

The invention claimed is:

1. A 6-(halomethyl)-1,2-benzisoxazol-3(2H)-one derivative represented by the formula:

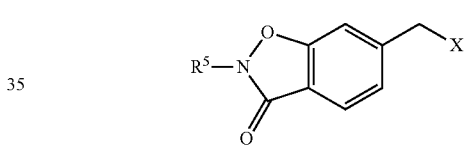

wherein $R^5$ is a methyl group that is substituted with one or more optionally substituted phenyl groups, or an optionally substituted oxygen-containing heterocyclic group; and X is a halogen atom.

2. A 6-(halomethyl)-1,2-benzisoxazol-3(2H)-one derivative according to claim 1, wherein X is a chlorine atom.

3. A 6-(halomethyl)-1,2-benzisoxazol-3(2H)-one derivative according to claim 1, wherein X is a bromine atom.

4. A 6-(halomethyl)-1,2-benzisoxazol-3(2H)-one derivative according to claim 1, wherein $R^5$ is an optionally substituted triphenylmethyl group.

5. A 6-(halomethyl)-1,2-benzisoxazol-3(2H)-one derivative according to claim 2, wherein $R^5$ is an optionally substituted triphenylmethyl group.

6. A 6-(halomethyl)-1,2-benzisoxazol-3(2H)-one derivative according to claim 3, wherein $R^5$ is an optionally substituted triphenylmethyl group.

7. A 6-(halomethyl)-1,2-benzisoxazol-3(2H)-one derivative according to claim 1, wherein $R^5$ is an optionally substituted tetrahydro-2H-pyran-2-yl group.

8. A 6-(halomethyl)-1,2-benzisoxazol-3(2H)-one derivative according to claim 2, wherein $R^5$ is an optionally substituted tetrahydro-2H-pyran-2-yl group.

9. A 6-(halomethyl)-1,2-benzisoxazol-3(2H)-one derivative according to claim 3, wherein $R^5$ is an optionally substituted tetrahydro-2H-pyran-2-yl group.

* * * * *